US008288369B2

(12) United States Patent
Malafa et al.

(10) Patent No.: US 8,288,369 B2
(45) Date of Patent: Oct. 16, 2012

(54) DELTA-TOCOTRIENOL TREATMENT AND PREVENTION OF PANCREATIC CANCER

(75) Inventors: Mokenge P. Malafa, Tampa, FL (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 781 days.

(21) Appl. No.: 11/768,373

(22) Filed: Jun. 26, 2007

(65) Prior Publication Data

US 2008/0004233 A1    Jan. 3, 2008

Related U.S. Application Data

(60) Provisional application No. 60/805,916, filed on Jun. 27, 2006.

(51) Int. Cl.
*A61K 31/355* (2006.01)
*A61K 31/513* (2006.01)
*A61K 31/7052* (2006.01)
*A61K 31/7105* (2006.01)
*A61P 35/00* (2006.01)

(52) U.S. Cl. ......... 514/183; 514/274; 514/458; 435/374
(58) Field of Classification Search .................. None
See application file for complete search history.

(56) References Cited

U.S. PATENT DOCUMENTS

| 5,919,818 | A | 7/1999 | Lane et al. | |
| 6,239,114 | B1* | 5/2001 | Guthrie et al. | 514/32 |
| 6,441,029 | B1 | 8/2002 | Elson | |
| 2003/0007961 | A1 | 1/2003 | Wilburn | |
| 2004/0023894 | A1* | 2/2004 | Hasler-Nguyen et al. | 514/27 |
| 2006/0088870 | A1* | 4/2006 | Finkelstein et al. | 435/6 |
| 2007/0134681 | A1 | 6/2007 | Liew et al. | |
| 2007/0154576 | A1 | 7/2007 | Tripp et al. | |

FOREIGN PATENT DOCUMENTS

| WO | 99/15167 A2 | 4/1999 |
| WO | 01/51043 A2 | 7/2001 |
| WO | 01/58889 A1 | 8/2001 |
| WO | 02/080854 A2 | 10/2002 |
| WO | 03/053407 A1 | 7/2003 |

OTHER PUBLICATIONS

Blaylock (Natural Strategies for Cancer Patients, 2003). p. 170.*
Neoptolemos et al. (N. Engl. J. Med. 2004; 350: 1200-10).*
PTAK Wellness. Electronic Resource. Available online Nov. 7, 2004. www.ptakrx4health.com/product_info.php/products_id/146.*
Giovanetti et al. Synergistic cytotoxicity and pharmacogenetics of gemcitabine and pemetrexed combination in pancreatic cancer cell lines. Clin. Cancer Res. 2004; 10: 2936-2943, Published online May 6, 2004.*
Merck Manual: Home Edition. titled: Combinaton therapy. Chabner et al. Aug. 2007. Electronic Resource: [http://merck.com/mmhe/sec15/ch182/ch182h.html]. Retrieved online on Sep. 11, 2010.*
Shah, S. J. et al. 2005. "Gamma-Tocotrienol Inhibits Neoplastic Mammary Epithelial Cell Proliferation by Decreasing Akt and Nuclear Factor KappaB Activity." Society for Experimental Biology and Medicine. pp. 235-241.
Sylvester, P. W. et al. 2002. "Antioxidants in Dietary Oils: Their Potential Role in Breast Cancer Prevention." Mal. J. Nutr. vol. 8. No. 1. pp. 1-11.
Goh, et al., Inhibition of Tumour Promotion by Various Palm-Oil Tocotrienols, Int. J. Cancer, 1994, vol. 57, pp. 529-531.
Oettle, et al., Gemcitabine in Combination With 5-Fluorouracil With or Without Folinic Acid in the Treatment of Pancreatic Cancer, Cancer Supplement, 2002, vol. 95, No. 4, pp. 912-922.
Vraka, et al., Synthesis and Study of the Cancer Cell Growth Inhibitory Properties of Alpha-, Gamma-Tocopheryl and Gamma-Tocotrienyl 2-Phenylselenyl Succinates, Bioorganic & Medicinal Chemistry, 2006, vol. 14, pp. 2684-2696.
Yu, et al., Compare the Preventive Effect of Alpha-Tocopherol, Alpha-, Gamma-, and Delta-Tocotrienols on the Formation of Aflatoxin B1 (AFB1) Epoxide and the Potential to Prevent Liver Cancer Carcinogenesis at the Initiation, Proc. Am. Assoc. Cancer Res. Ann. Meeting, 2007, Los Angeles, CA.
Wali, et al., The Synergistic Inhibitory Effect of Combined Statin and Gamma-Tocotrienol Treatment on the Growth of the Highly Malignant +SA Mammary Epithelial Cells in Culture is Mediated Through the Inhibition of MAPK and Akt Mitogenic Signaling, Proc. Am. Assoc. Cancer Res. Ann. Meeting, 2007, Los Angeles, CA.
Ahn, et al., Gamma-Tocotrienol Inhibits Nuclear Factor-KappaB Signaling Pathway Through Inhibition of Receptor-Interacting Protein and TAK1 Leading to Suppression of Antiapoptotic Gene Products and Potentiation of Apoptosis, The Journal of Biological Chemistry, 2007, vol. 282, No. 1, pp. 809-820.
Neuzil, et al., Vitamin E Analogs, a Novel Group of "Mitocans," as Anticancer Agents: The Importance of Being Redox-Silent, Molecular Pharmacology, 2007, vol. 71, No. 5, pp. 1185-1199.
Jemal, A., et al., Cancer statistics, 2006. CA Cancer J Clin, 2006. 56(2): p. 106-30.
Lippman, S.M. and B. Levin. Cancer prevention: strong science and real medicine. J Clin Oncol, 2005. 23(2): p. 249-53.
Agarwal et al. 2004. "Tocotrienol-Rich Fraction of Palm Oil Activates p53, Modulates Bax/Bcl2 Ratio and Induces Apoptosis Independent of Cell Cycle Association." Cell Cycle. vol. 3. No. 2. pp. 205-211.
Ghaneh et al. 2001. "Adenovirus-Mediated Transfer of p53 and p16(INK4a) Results in Pancreatic Cancer Regression in Vitro and in Vivo." Gene Ther. vol. 8. No. 3. pp. 199-208.
Kimura et al. 1997. "Inability to Induce the Alteration of Tumorigenicity and Chemosensitivity of p53-Null Human Pancreatic Carcinoma Cells After the Transduction of Wild-Type p53 Gene." Anticancer Res. vol. 17. No. 2A. pp. 879-883.

(Continued)

*Primary Examiner* — Brandon Fetterolf
*Assistant Examiner* — Anna Pagonakis
(74) *Attorney, Agent, or Firm* — Robert Varkonyi; Smith & Hopen, P.A.

(57) ABSTRACT

Methods are disclosed for treating neoplastic disorders, such as pancreatic cancer, using tocotrienols; namely, gamma-tocotrienol and delta tocotrienol. The antitumorogenic effects of these compounds are shown both in vitro and in vivo using several human pancreatic cancer cell lines and MIA-PACA2 human pancreatic cancer cells xenografted in nude mice. Also disclosed are methods of testing the efficacy of potential chemotherapeutic agents by measuring their effect on surrogate endpoint biomarkers, such as Ki-67 and p27. Associated compounds are also disclosed.

9 Claims, 38 Drawing Sheets

OTHER PUBLICATIONS

Mayo Foundation for Medical Education and Research. 1998-2010. "Pancreatic Cancer: Causes." MayoClinic.com. http://www.mayoclinic.com/health/pancreatic-cancer/DS00357/DSECTION=causes accessed Sep. 10, 2010.

Mayo Foundation for Medical Education and Research. 1998-2010. "Pancreatic Cancer: Risk Factors." MayoClinic.com. http://www.mayoclinic.com/health/pancreatic-cancer/DS00357/DSECTION=risk-factors accessed Sep. 10, 2010.

Pancreatic Cancer Action Network 2010. "Learn About Pancreatic Cancer: Risk Factors for Pancreatic Cancer." http://www.pancan.org/section_facing_pancreatic_cancer/learn_about_pan_cancer/rish_factors accessed Sep. 10, 2010.

Rodicker et al. 2003. "p73 Is Effective in p53-Null Pancreatic Cancer Cells Resistant to Wilt-Type TP53 Gene Replacement." Cancer Research. vol. 63. pp. 2737-2741.

Schwartz et al. 1993. "p53 in the Anticancer Mechanism of Vitamin E." Oral Oncol. Eur. J. Cancer. vol. 29B. No. 4. pp. 313-318.

Srivastava et al. 2006. "Tocotrienol-Rich Fraction of Palm Oil Induces Cell Cycle Arrest and Apoptosis Selectively in Human Prostate Cancer Cells." Biochemical and Biophysical Research Communications. vol. 346. pp. 447-453.

Richards. 2008. "Tocotrienols—A Multi-Dimensional Nutrient Powerhouse." http://www.wellnessresources.com/tips/articles/tocotrienols_a_multi_dimensional_nut accessed Jul. 16, 2010.

HDAC Inhibitors base. 2010. "CI-994." http://www.hdacis.com/tacedinaline.html accessed on Aug. 15, 2011.

\* cited by examiner

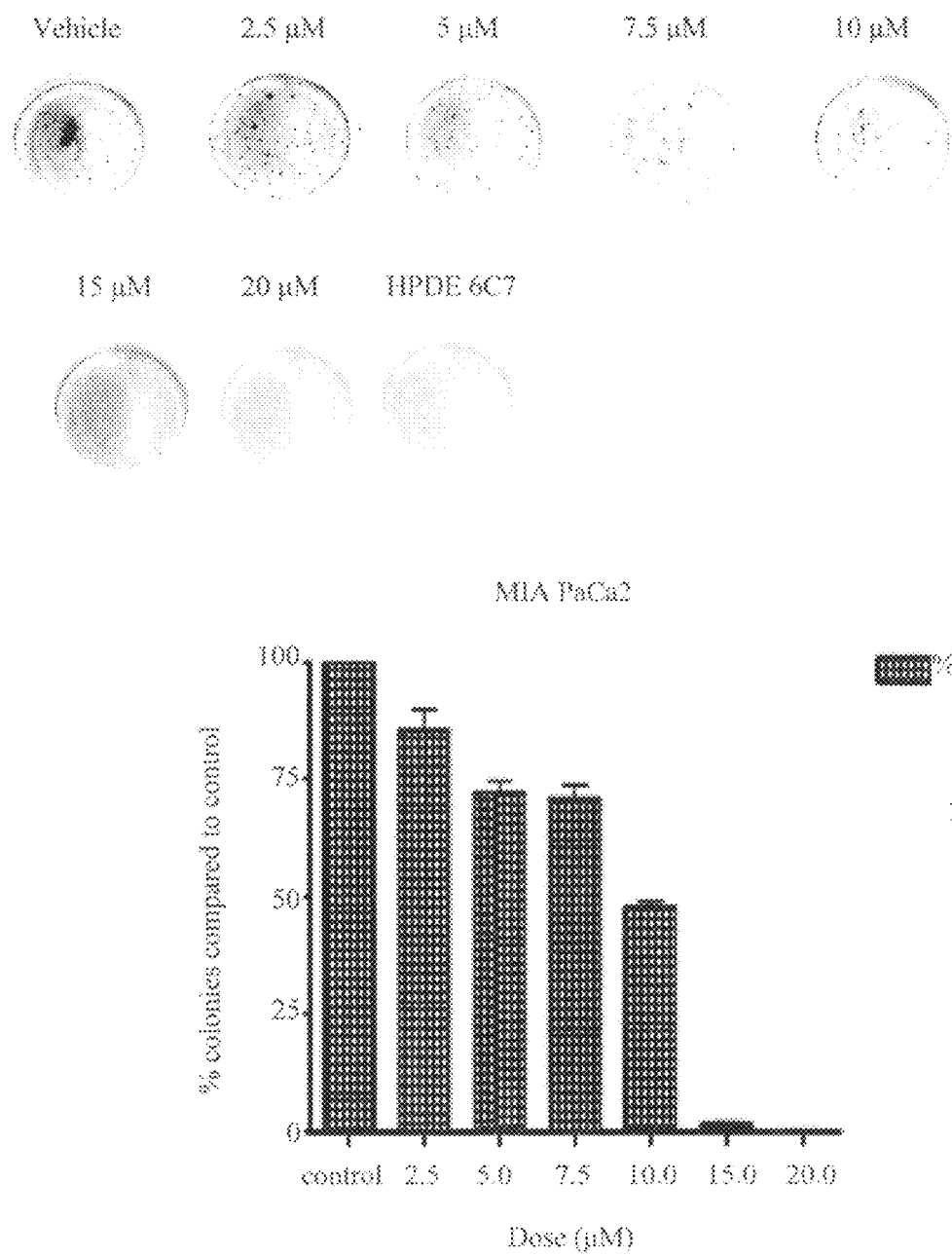

| Time (Hrs) | 0 | 6 | 12 | 24 | 48 |

MIA PaCa2

BXPC3

SW 1990

HPDE

V = viable tumor
N = Area of tumor necrosis
% = percent positive staining

|          | 24h | 48h |
|----------|-----|-----|
| Control  | 100 | 100 |
| Vehicle  | 101 | 102 |
| alpha T3 | 121 | 116 |
| beta T3  | 99  | 68  |
| gamma T3 | 107 | 89  |
| delta T3 | 97  | 83  |
| alpha T  | 122 | 107 |
| gamma T  | 116 | 94  |
| TS       | 110 | 104 |
| GG       | 92  | 83  |
| SA       | 109 | 105 |

|  | 24h | 48h |
|---|---|---|
| Control | 100 | 100 |
| Vehicle | 95 | 101 |
| alpha T3 | 116 | 93 |
| beta T3 | 79 | 61 |
| gamma T3 | 66 | 37 |
| delta T3 | 77 | 67 |
| alpha T | 111 | 86 |
| gamma T | 121 | 81 |
| TS | 96 | 76 |
| GG | 82 | 53 |
| SA | 105 | 90 |

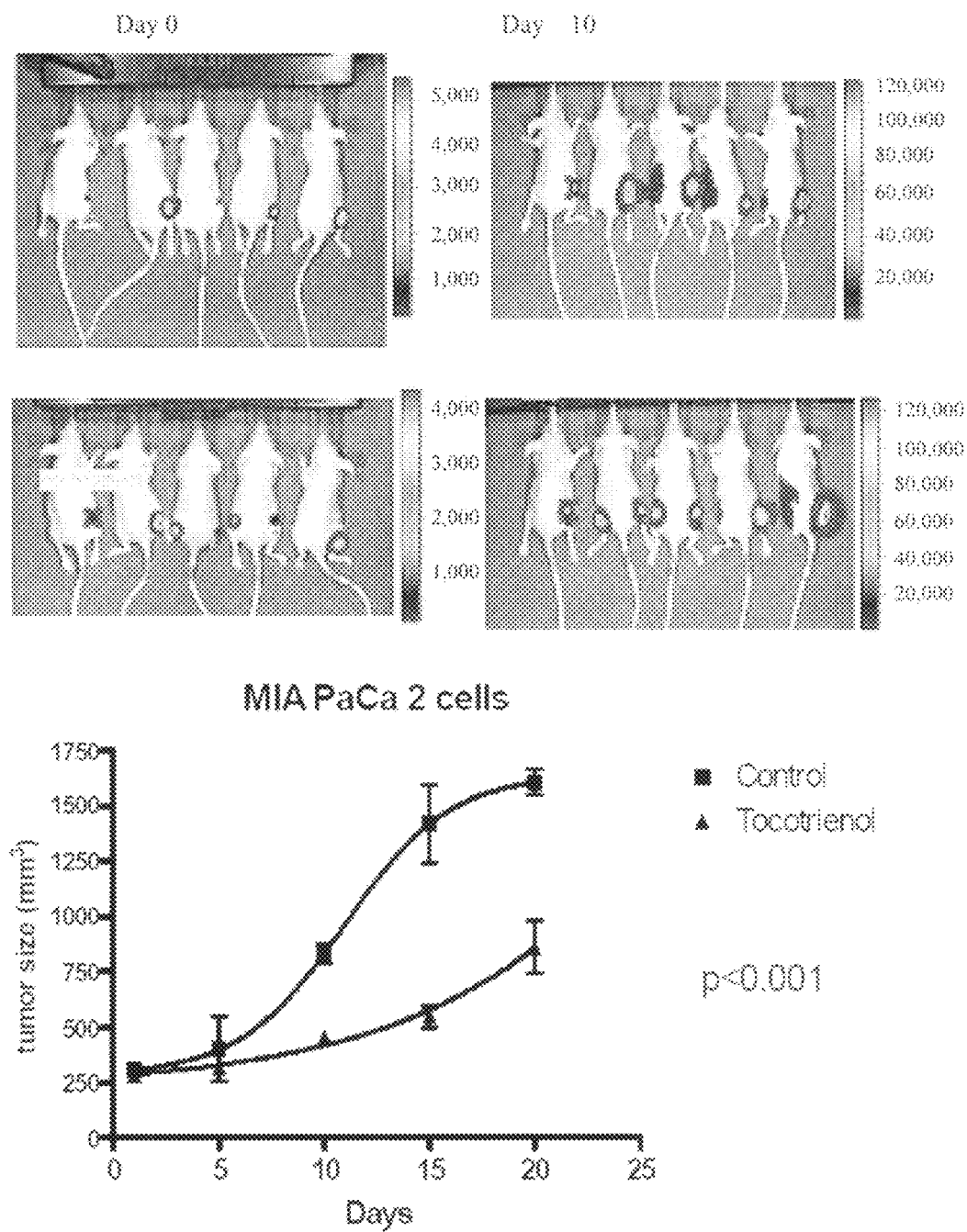

DELTA-TOCOTRIENOL TREATMENT AND PREVENTION OF PANCREATIC CANCER

CROSS REFERENCE TO RELATED APPLICATIONS

This application is a non-provisional application of co-pending U.S. Provisional Application, No. 60/805,916, filed Jun. 27, 2006; which is fully incorporated herein by reference.

STATEMENT OF GOVERNMENT INTEREST

This invention was made with Government support under Grant No. DAMD 17-01-1-04 awarded by the Department of Defense, and NCI Grant No. 3R01CA098473-03S1. The Government has certain rights in the invention.

BACKGROUND OF THE INVENTION

The pancreas is an extremely common site for the development of early neoplasms-noninvasive clonal epithelial expansions. In a minority of persons, these clones of cells serially acquire genetic changes that can lead to an invasive adenocarcinoma. Pancreatic cancer, once invasive, is almost uniformly fatal. The epithelial cells in the advanced stage of this process are very aggressive, seemingly having an innate capability for metastasis that is exhibited rather soon after they invade beyond the duct structure into surrounding tissue. In order to alleviate the dismal prognosis associated with this disease, it is imperative that the process of pancreatic carcinogenesis be recognized and treated prior to invasion. Chemoprevention is the administration of agents (drugs, biologics, and nutrients) to slow progression of, reverse, or inhibit carcinogenesis thereby lowering the risk of developing invasive or clinically significant disease. Understanding the morphology and biology of precursor lesions of invasive pancreatic cancer has therefore become an issue of paramount importance. In the last decade, significant progress has been made in the recognition and appropriate classification of these precursor lesions. Mucinous cystic neoplasms (MCNs), intraductal papillary mucinous neoplasms (IPMNs), and pancreatic intraepithelial neoplasia (PanIN) encompass the three known morphologically distinct precursors to invasive pancreatic cancer.

A large number of case-control and cohort studies have shown that there is a significant clustering of pancreatic cancer in some families. These high-risk inherited pancreatic cancers are estimated to represent about 10% of pancreatic cancers. Five well-known genetic syndromes with known gene defects account for approximately 20% of the families in which there is aggregation of pancreatic cancer. These syndromes include (1) BRCA2, (2) familial atypical multiple mole melanoma (p16/CDKN2A), (3) Peutz-Jeghers Syndrome; (4) HNPCC; and (5) familial pancreatitis. Majority of pancreatic cancers are sporadic and have evidence of widespread chromosomal instability, including a high rate of translocations and deletions. Nearly all (>90%) preinvasive lesions have an early mutation in the K-Ras protein involved in the transmission of growth factor signals. In the middle stages of preinvasive progression >90% of lesions develop inactivation of the CDKN2A (p16) cyclin dependent kinase inhibitor. In later stages most preinvasive lesions also harbor mutations of the TP53 (p53) and in MADH4, the common Smad protein involved in transduction of TGFβ and activin signals. Despite the enormous obvious benefit for chemopreventive agents in pancreatic neoplasia, direct drug investigations for chemopreventive indications have been slow to emerge. A critical factor is the challenge of conducting studies that will define and demonstrate clinical benefit.

Proliferation of pancreatic cancer is regulated through aberrant oncogenic Ras signaling and its effect on cyclin kinase inhibitors such as $p27^{kip1}$. Previous studies have demonstrated that pharmacologic inhibition of one of the ras signaling pathways, the Raf-MEK-ERK pathway, elicits pancreatic cancer cell cycle arrest through induced expression of p27 (Cancer Res 2005; 65(11):4870-80). Tocotrienols, the chemical form of vitamin E with an unsaturated isoprenoid side chain, are receiving attention as promising dietary supplements for cancer prevention and treatment.

Tocotrienols are the primary form of vitamin E in the seeds of most monocot plants such as palm and cereals such as rice and wheat. The biosynthesis of tocotrienols and tocopherols occur exclusively in photosynthetic organisms and arise from homogentisic acid. Tocotrienols arise from the condensation of homogentisic acid and geranylgeranyl diphosphate while the committed step in tocopherol synthesis is the condensation of homogentisic acid and phytyl diphosphate. Structurally tocopherols and tocotrienols share some resemblance consisting of a common chromanol head and a side chain at the C-2 position however, their side chains distinguish tocopherols and tocotrienols.

While tocopherol has a saturated phytyl tail, tocotrienol possesses an unsaturated isoprenoid side chain. Tocopherols and tocotrienols are further separated into individual compounds assigned by the greek letter prefixes ($\alpha,\beta,\gamma,\delta$) depending on the number and position of methyl substitution on the chromanol ring. As reflected in their structural similarity, tocopherols and tocotrienols are well recognized for their antioxidant effect. However, tocotrienols are the group of natural vitamin E compounds with clear and consistent antitumor activity. Semisynthetic tocopherols such as tocopherol succinate have antitumor activity however the bioavailability of the intact compound after oral consumption is poor making it unsuitable for chemopreventive interventions. Structure activity studies of the proapoptotic effects of vitamin E compounds have clearly documented the importance of the unsaturated isoprenoid tail of the vitamin E compounds in their antitumor bioactivity. Furthermore, these studies indicate that decreasing the number of methyl substitutions on the chromanol ring, is associated with increasing antitumor potency.

SUMMARY OF INVENTION

In one embodiment, the invention includes a method of determining the effectives of a chemotherapeutic agent by determining, in an isolated sample, a first level of a surrogate endpoint biomarker such as p27. The sample is then contacted with an experimentally effective amount of the chemotherapeutic agent being tested. After the chemotherapeutic agent has been administered, a second level of the surrogate endpoint biomarker is taken and compared to the first (pre-treatment) level. The candidate chemotherapeutic agent demonstrates effectiveness where the second (post-treatment) level of p27 is increased to a statistically significant degree over the pre-treatment and/or control levels.

In another embodiment, the invention provides a method of determining the effectiveness of a chemotherapeutic agent by further determining, in the isolated sample, a first level of a second surrogate endpoint biomarker such as Ki-67 and/or p-MAPK. After the chemotherapeutic agent has been administered, a second level of Ki-67 and/or p-MAPK is taken and compared to the first (pre-treatment) level and/or a control. The candidate chemotherapeutic agent demonstrates effectiveness where the second (post-treatment) level of Ki-67 and/or p-MAPK is decreased to a statistically significant degree below the pre-treatment and/or control levels.

Another embodiment of the invention includes a method of screening for pancreatic ductal carcinoma, or a stage of pancreatic cancer in a subject by determining, such as in an isolated sample, the level of a biomarker; namely, p27. The level of the biomarker is then compared to a corresponding control level in one or more control samples. In a preferred embodiment the control samples are obtained from individuals who have been determined not to have pancreatic ductal carcinoma, or a stage of pancreatic cancer.

The determination of a statistically significant similarity between the level of the biomarker in the subject and the level of the biomarker in the control sample(s) is indicative of the lack of pancreatic ductal carcinoma, or a stage of pancreatic cancer in the subject. A statistically significant decrease in the level of p27 in the subject, compared to the level of the biomarker in the control sample(s), indicates the presence of pancreatic ductal carcinoma, or a stage of pancreatic cancer in the subject.

In an alternate embodiment, the level of a second biomarker, namely Ki-67 and/or p-MAPK, is determined and compared to a control level of Ki-67 and/or p-MAPK in one or more control samples. A statistically significant increase between the level of Ki-67 and/or p-MAPK in the subject and the control sample(s) is indicative of pancreatic ductal carcinoma, or a stage of pancreatic cancer in the subject. A statistically significant similarity in the level of Ki-67 and/or p-MAPK in the subject, compared to the control sample(s), is indicative of the lack of pancreatic ductal carcinoma, or a stage of pancreatic cancer in the subject.

Methods of determining the level of the biomarker in the subject and control sample(s) are known to the ordinary practitioner. In one embodiment, as an example, the level of the biomarker is determined utilizing an antibody which binds the biomarker. The sample containing the biomarker is contacted with the antibody under conditions which allow binding of the biomarker to the antibody; the presence of the biomarker can then be quantified.

The invention also includes compositions useful in performing the associated methods. For example, the invention includes a composition comprising a plurality of isolated proteins which bind selectively to the protein products of the associated biomarkers; namely, Ki-67 and/or p-MAPK, and p27. In a preferred embodiment, the isolated proteins selectively amplify complementary double stranded DNA. A composition is also included comprising a plurality of biomarker specific primers, wherein each biomarker specific primer selectively amplifies double stranded DNA complementary to a unique biomarker such as Ki-67, p-MAPK, and p27. Alternatively, the invention includes a composition comprising a plurality of isolated proteins which bind selectively to the protein products of at least two unique biomarkers, wherein each unique biomarker is selected from the group consisting of Ki-67, p-MAPK and p27.

Accordingly, the invention includes method of treating cancer, such as pancreatic ductal carcinoma, or a stage of pancreatic cancer, by administering to a subject a composition comprising a therapeutically effective amount of a tocotrienol. In a preferred embodiment the tocotrienol is gamma-tocotrienol and/or delta-tocotrienol, which is administered as a pharmaceutical composition. The composition of the preferred embodiment is substantially free of alpha-tocotrienol, beta-tocotrienol and/or tocopherols. Although one of ordinary skill will recognize methods of determining the appropriate dose, the composition of one embodiment comprises between about 100 mg and 300 mg tocotrienol which is administered twice daily.

The tocotrienol of the preferred embodiment has the formula:

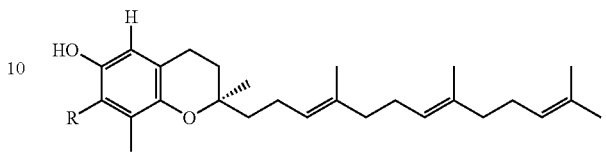

wherein R is selected from the group consisting of H and $CH_3$.

BRIEF DESCRIPTION OF THE DRAWINGS

For a fuller understanding of the nature and objects of the invention, reference should be made to the following detailed description, taken in connection with the accompanying drawings, in which:

FIG. 1A is an image of MIA PaCa2 cells in soft agar; significant inhibition of anchorage independent growth of cells occurred when treated with weekly δ-tocotrienol compared to vehicle.

FIG. 12A MIA PaCa2 xenografts in nude mice were measured every second day for tumor growth. Mice were treated with either rice bran oil (vehicle) or δ-tocotrienol (100 mg/kg/day) via gavage five times per week. Results demonstrate significant inhibition of pancreatic tumor growth in mice treated with δ-tocotrienol.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

δ-Tocotrienol Inhibits Pancreatic Cancer Cells In Vitro.

In one embodiment, the invention includes a method whereby δ-tocotrienol inhibits pancreatic tumor growth, blocks malignant transformation, and induces apoptosis in vitro. Here, the inventors show the antitumorigenic properties of δ-tocotrienol in vitro. Human pancreatic ductal carcinoma cell lines (MIA PaCa2, SW1990, BXPC3) from American type tissue culture (ATTC, Rockville, Md.) were acquired, grown at 70% confluency per protocol, and treated with δ-tocotrienol. Immortalized human pancreatic ductal epithelial cells, HPDE 6C7, were treated under identical conditions to investigate δ-tocotrienol's selective effects on pancreatic cancer cells. Results show that δ-tocotrienol selectively inhibits transformation and proliferation.

MIA PaCa2, SW1990, BXPC3, and HPDE 6C7 cells were treated with increasing concentrations of δ-tocotrienol. FIG. 1A shows significant inhibition of anchorage independent growth of MIA PaCa2 cells in soft agar when treated with weekly δ-tocotrienol compared to vehicle. HPDE 6C7 cells grown in recommended media alone did not undergo transformation in soft agar, as would be expected in this preneoplastic cell line, and served as our negative control.

Figure 1B:
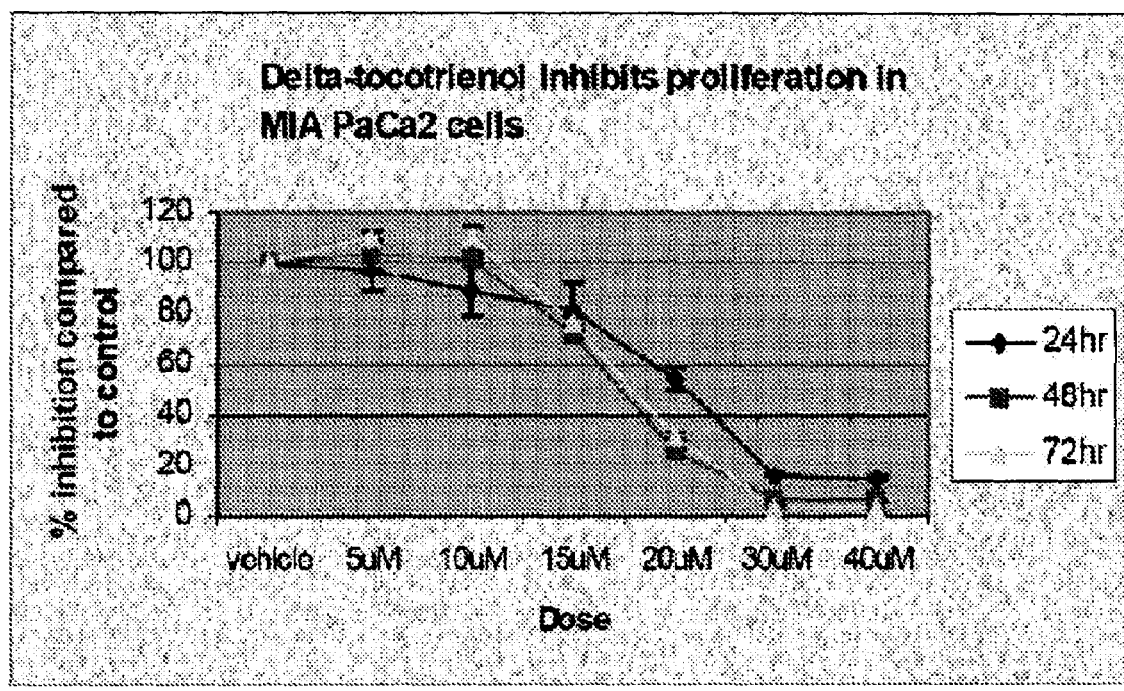
FIG. 1B is a graph wherein MIA PaCa2 pancreatic cancer cells ($3 \times 10^3$) were plated in 96 well plates and treated the following day with δ-tocotrienol. Proliferation was assessed by MTT at 24 hour intervals. Results show a dose dependent inhibition of proliferation. The $IC_{50}$ for all three pancreatic cancer cell lines was 20-25 μM at 24 hours. HPDE 6C7 cells were also treated with increasing concentrations of δ-tocotrienol for 24 hours.
Figure 1C:
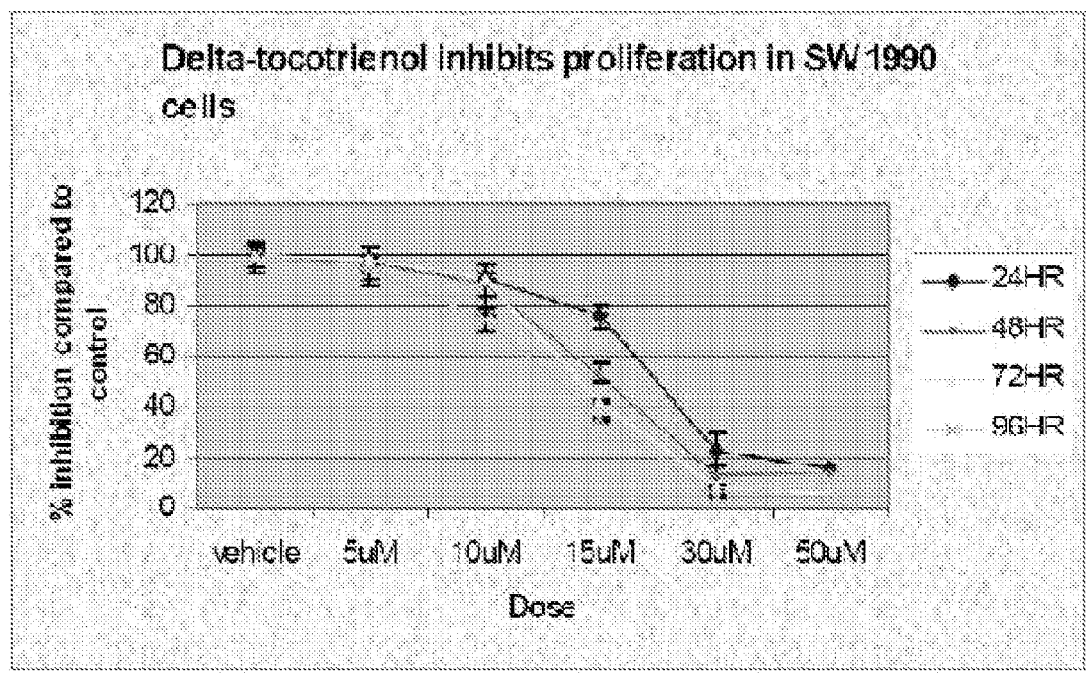
FIG. 1C is a graph wherein SW1990 pancreatic cancer cells ($3 \times 10^3$) were plated in 96 well plates and treated the following day with δ-tocotrienol. Proliferation was assessed by MTT at 24 hour intervals. Results show a dose dependent inhibition of proliferation. The $IC_{50}$ for all three pancreatic cancer cell lines was 20-25 μM at 24 hours. HPDE 6C7 cells were also treated with increasing concentrations of δ-tocotrienol for 24 hours.
Figure 1D:
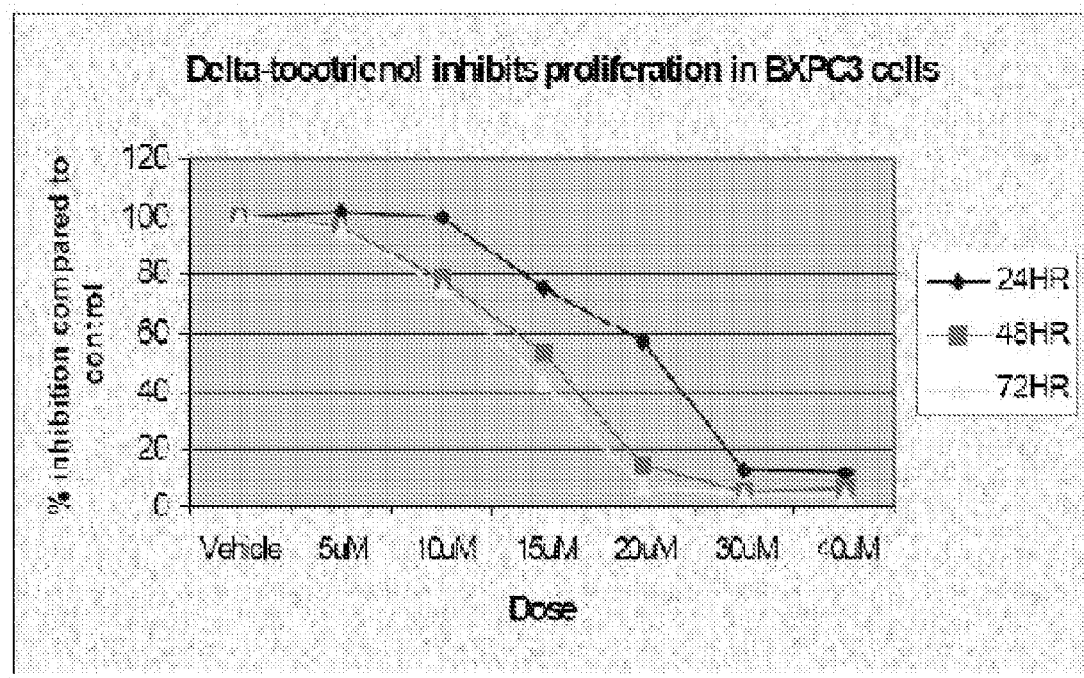
FIG. 1D is a graph wherein BXPC3 pancreatic cancer cells ($3 \times 10^3$) were plated in 96 well plates and treated the following day with δ-tocotrienol. Proliferation was assessed by MTT at 24 hour intervals. Results show a dose dependent inhibition of proliferation. The $IC_{50}$ for all three pancreatic cancer cell lines was 20-25 μM at 24 hours. HPDE 6C7 cells were also treated with increasing concentrations of δ-tocotrienol for 24 hours.
Figure 1E:
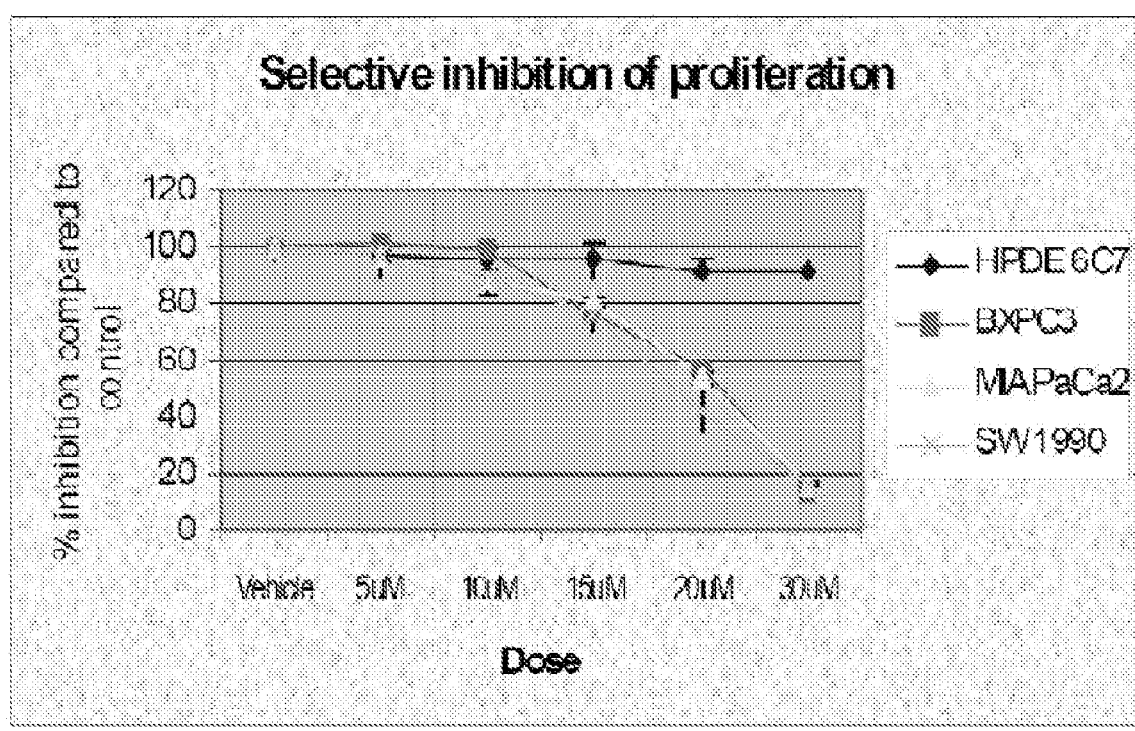
FIG. 1E is a graph showing selective inhibition of proliferation of pancreatic cancer cell lines by δ-tocotrienol at 24 hours. HPDE 6C7 cells were relatively resistant to the antiproliferative effects of tocotrienol, even at the highest concentrations.

Pancreatic cancer cells ($3 \times 10^3$) were plated in 96 well plates and treated the following day with δ-tocotrienol. Proliferation was assessed by MTT at 24 hour intervals. Results show a dose dependent inhibition of proliferation (FIGS. 1B-1D). The $IC_{50}$ for all three pancreatic cancer cell lines was 20-25 µM at 24 hours. HPDE 6C7 cells were also treated with increasing concentrations of δ-tocotrienol for 24 hours. FIG. 1E shows selective inhibition of proliferation of pancreatic cancer cell lines by δ-tocotrienol at 24 hours. HPDE 6C7 cells were relatively resistant to the antiproliferative effects of tocotrienol, even at the highest concentrations.

The observed antiproliferative effect of δ-tocotrienol on pancreatic cancer cells likely occurs through cell cycle regulation. Results also show that δ-tocotrienol causes selective G1 cell cycle arrest and is associated with upregulation of the cyclin kinase inhibitor $p27^{kip1}$. MIA PaCa2, SW 1990, BXPC3 and HPDE 6C7 cells were treated with either δ-tocotrienol 20 µM or vehicle for 24 hours. Cells were harvested, washed twice in PBS, and fixed in ethanol overnight. Pellets were washed the following day in PBS, stained with propidium iodide, and analyzed by flow cytometry for cell cycle phase.

Figure 2A:
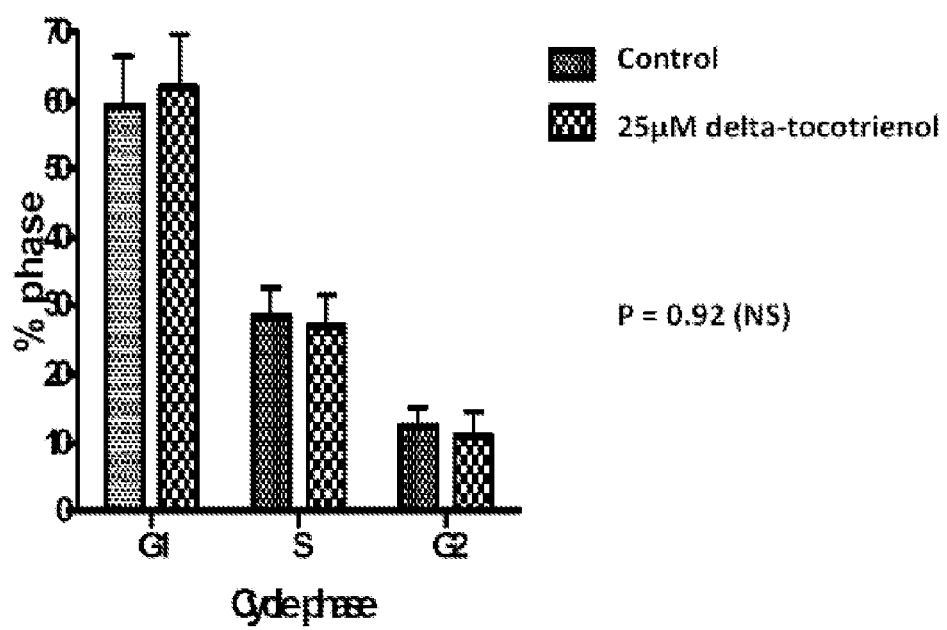
FIG. 2A is a graph showing significant G1 cell cycle arrest in HPDE 6C7 and SW1990 pancreatic cancer cell lines treated with δ-tocotrienol (25 μM). In contrast, δ-tocotrienol had no effect on cell cycle phase in immortalized human pancreatic ductal epithelial cells (HPDE 6C7).
Figure 2A:
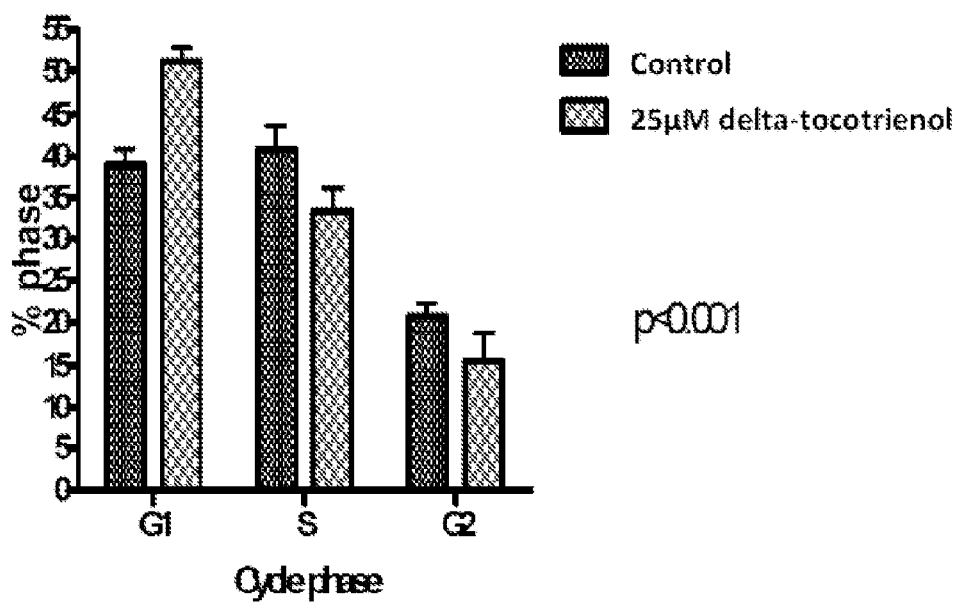
Figure 2B:
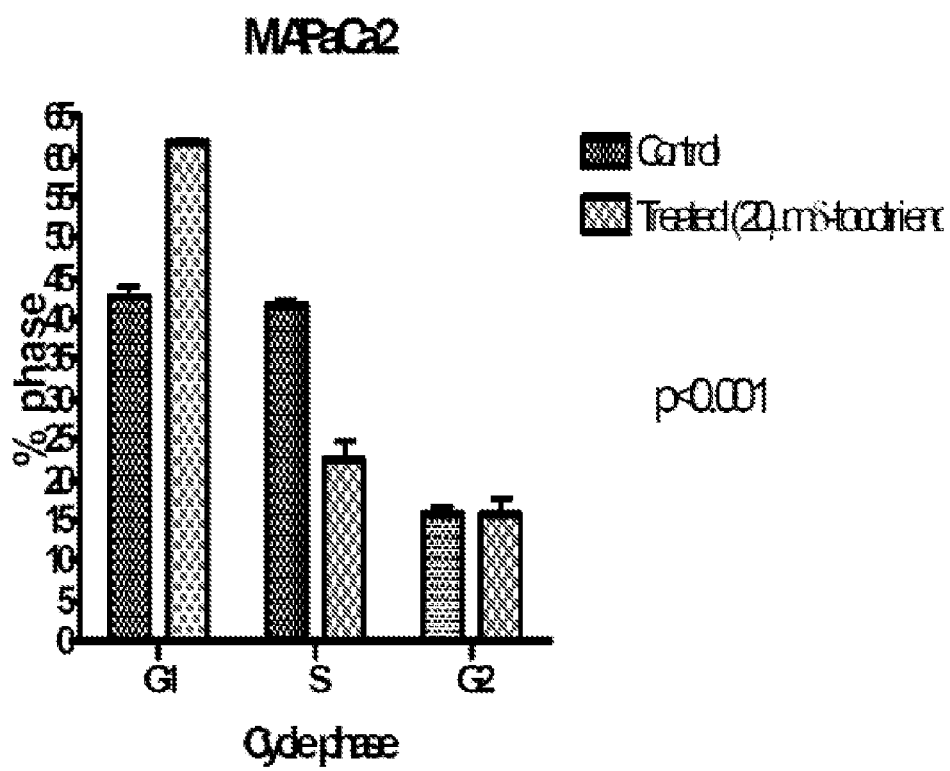
FIG. 2B is a graph showing significant G1 cell cycle arrest in MaPaCa2 and BXPC3 pancreatic cancer cell lines treated with δ-tocotrienol (20 μM). In contrast, δ-tocotrienol had no effect on cell cycle phase in immortalized human pancreatic ductal epithelial cells (HPDE 6C7).
Figure 2B:
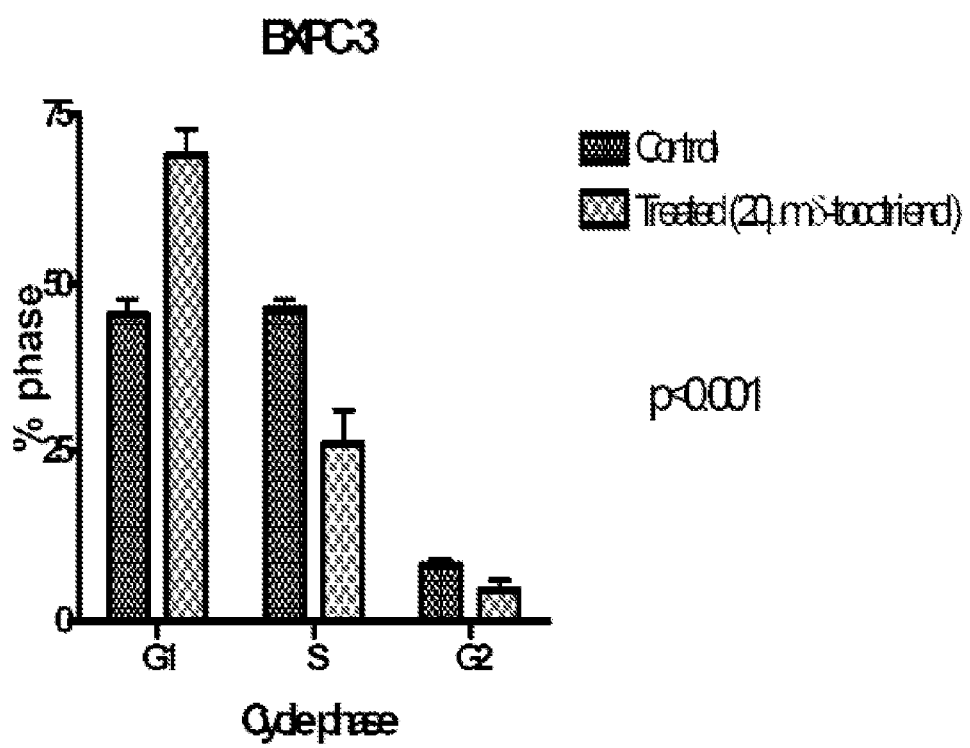
Figure 2C:
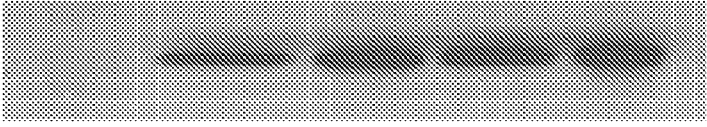
FIG. 2C is a series of blots showing a time dependent upregulation in p27$^{kip1}$ expression in all four pancreatic cancer cell lines. In contrast, a downregulation of p27$^{kip1}$ is seen in HPDE 6C7 cells treated with δ-tocotrienol.
Figure 2C:
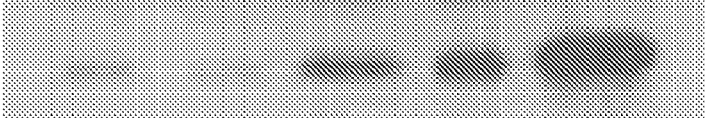
Figure 2C:
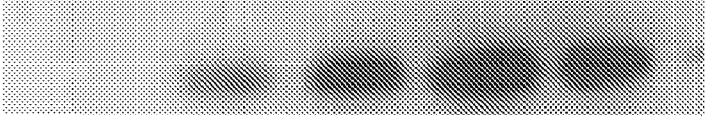
Figure 2C:
Figure 2D:
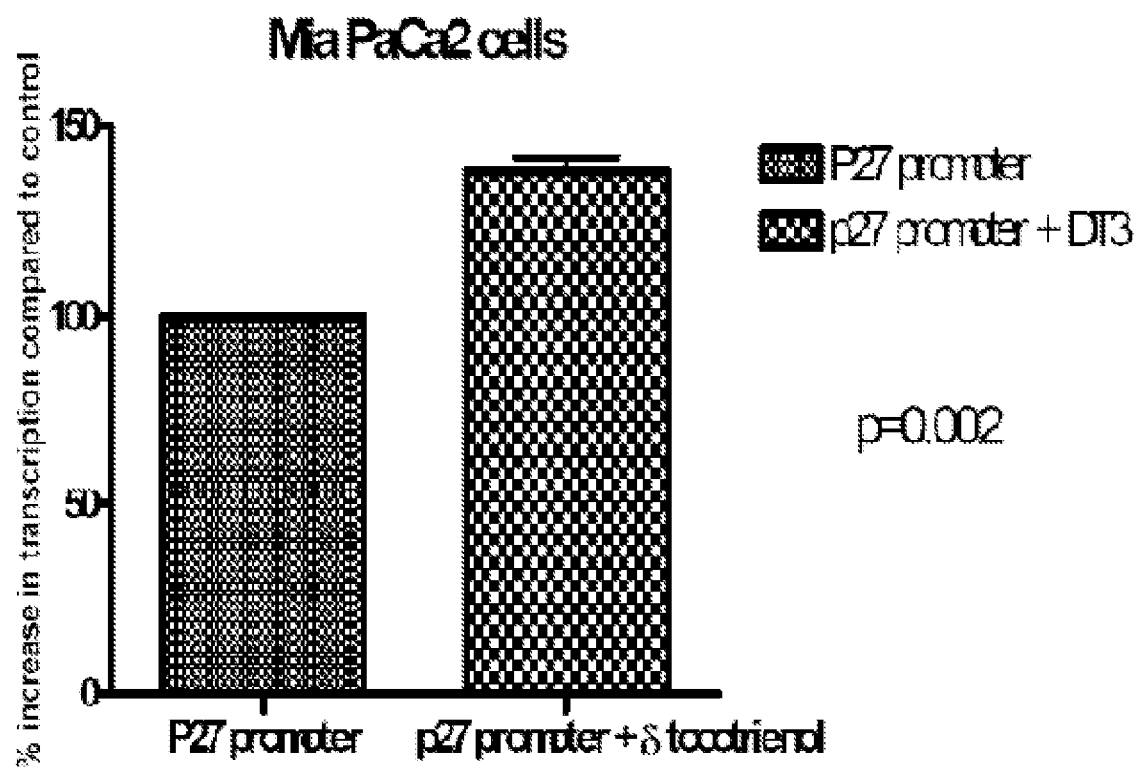
FIG. 2D is a graph showing an increase in luciferase activity in MIA PaCa2 cells treated with δ-tocotrienol.
Figure 2E:
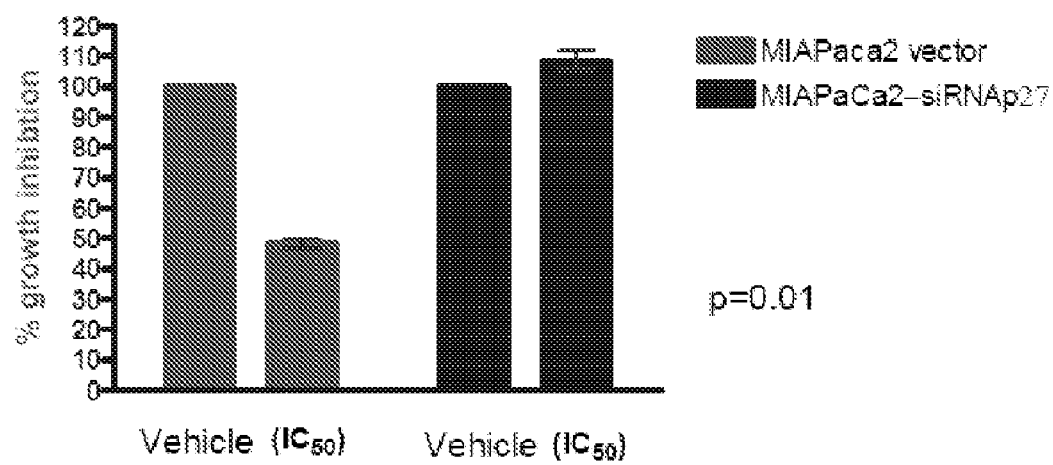
FIG. 2E is a graph and associated blots showing siRNAp27 rescues tocotrienol inhibition of pancreatic cancer cell growth.
Figure 2E:
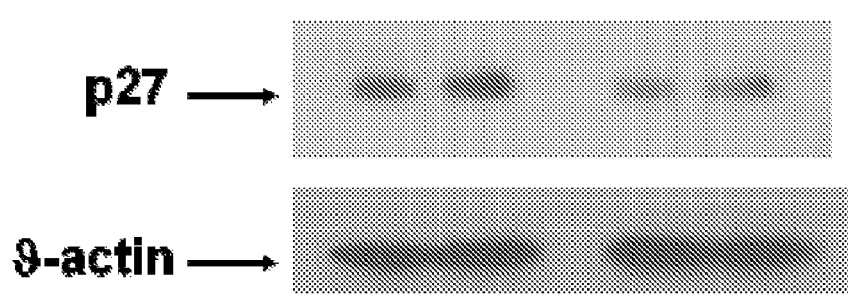
Figure 2F:
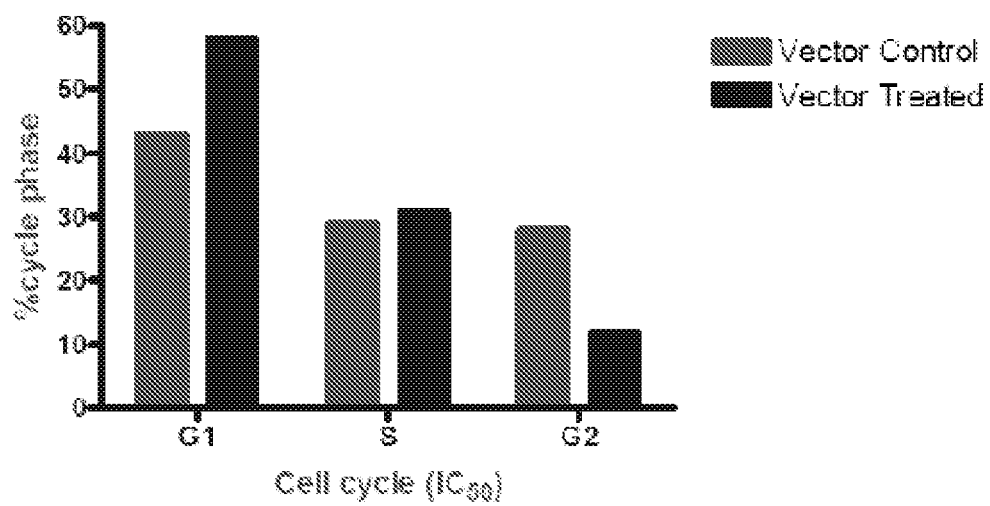
FIG. 2F is a pair of graphs showing that siRNAp27 rescues tocotrienol induced G1-S cell cycle arrest in pancreatic cancer cells.
Figure 2F:
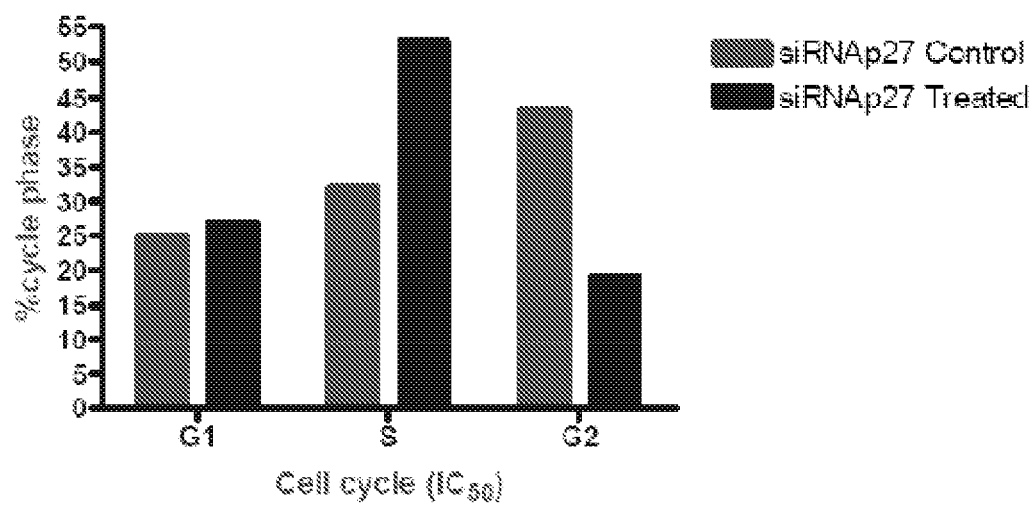

FIGS. 2A and 2B show significant G1 cell cycle arrest in all three pancreatic cancer cell lines treated with δ-tocotrienol. In contrast, δ-tocotrienol had no effect on cell cycle phase in immortalized human pancreatic ductal epithelial cells (HPDE 6C7). Important regulators of the G1 cell cycle phase include members of the cyclin kinase inhibitor family. One of these members, $p27^{kip1}$, appears to be important in the progression of pancreatic cancer. FIG. 2F shows that siRNAp27 rescues tocotrienol induced G1-S cell cycle arrest in pancreatic cancer cells.

Cell cycle inhibition by δ-tocotrienol was associated with altered protein expression of $p27^{kip1}$. The same 4 cell lines were treated with δ-tocotrienol (20 µM) and collected at progressive time intervals. Whole cell lysates were made from cell pellets washed twice in PBS and lysed in M-PER (Mammalian Protein Extraction Reagent, Pierce). Proteins from lysates were separated by SDS-PAGE and immunoblotted for $p27^{kip1}$ (BD Biosciences). FIG. 2C shows a time dependent upregulation in $p27^{kip1}$ expression in all three pancreatic cancer cell lines. In contrast, a downregulation of $p27^{kip1}$ is seen in HPDE 6C7 cells treated with δ-tocotrienol.

The mechanism by which δ-tocotrienol upregulates $p27^{kip1}$ protein expression was investigated using a luciferase reporter assay. Mia PaCa2 cells transfected with a $p27^{kip1}$ luciferase reporter (a gift from Dr. Pledger, Moffitt Cancer Center, Tampa) were treated with either δ-tocotrienol (20 µM) or vehicle for 24 hours. Luciferase activity was then measured using a luminometer. FIG. 2D shows an increase in luciferase activity in MIA PaCa2 cells treated with δ-tocotrienol. This suggests that δ-tocotrienol increases $p27^{kip1}$ protein expression through transcriptional upregulation. This dynamic is further demonstrated by the rescue of tocotrienol inhibition of MiaPaCa-2 cells by siRNAp27 (FIG. 2E).

δ-Tocotrienol was also shown to selectively inhibits downstream effectors of oncogenic Ras signaling. More than 80% of pancreatic cancers demonstrate abnormal oncogenic Ras signaling. The Ras effector pathways Raf-MEK-ERK and PI3 kinase-AKT are important for cell proliferation and survival, respectively. Data indicates that δ-tocotrienol has an inhibitory effect on oncogenic Ras signaling.

Figure 3A:
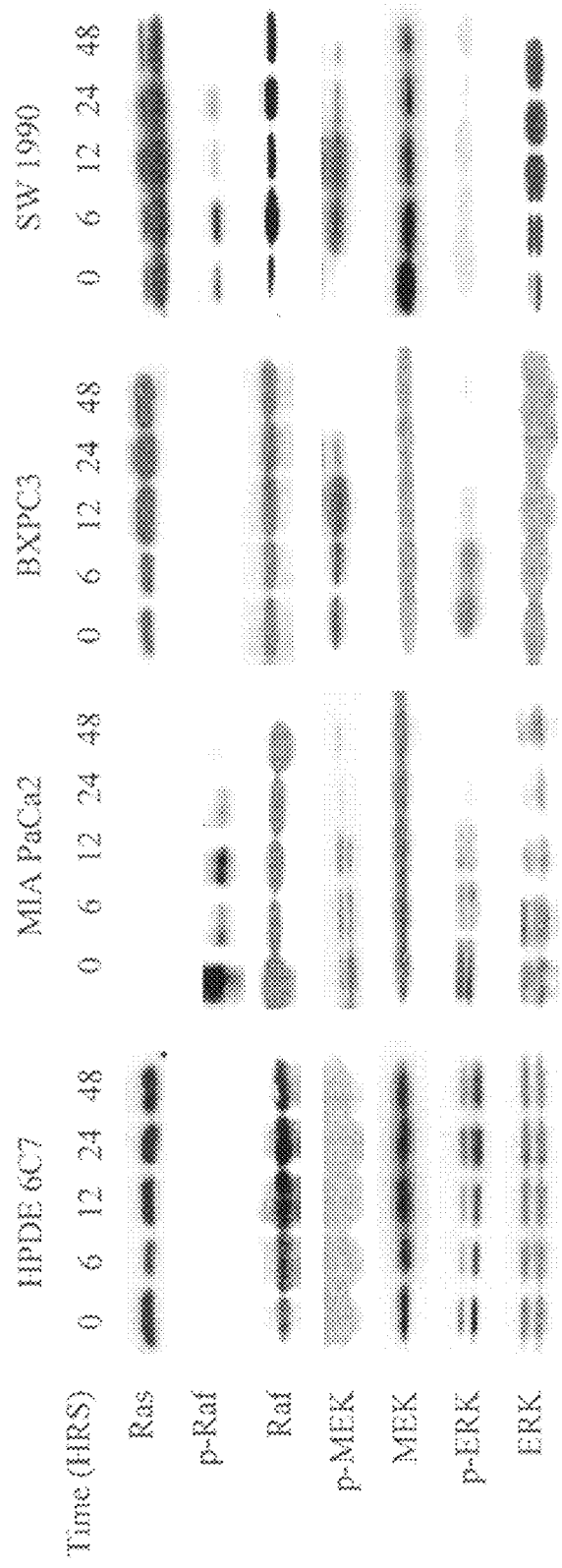
FIG. 3A is a blot series showing selective inhibition by δ-tocotrienol of the downstream phosphorylated targets of oncogenic Ras p-cRaf, p-MEK, and p-ERK. HPDE 6C7 cells were resistant to the inhibitory effects of δ-tocotrienol.

Pancreatic cancer cell lines (MIA PaCa2, SW1990, BXPC3) and HPDE 6C7 cells were treated with δ-tocotrienol (20 µM) and cell lysates were collected and prepared at progressive time intervals as described above. Proteins from lysates were run by SDS PAGE and immunoblotted with the following antibodies: Ras, p-cRaf (ser 338), p-MEK1/2, MEK1/2, pERK 44/42, ERK 44/42 (Cell Signaling) and c-Raf (BD Transduction Laboratories). FIG. 3A shows selective inhibition by δ-tocotrienol of the downstream phosphorylated targets of oncogenic Ras p-cRaf, p-MEK, and p-ERK.

Figure 3B:
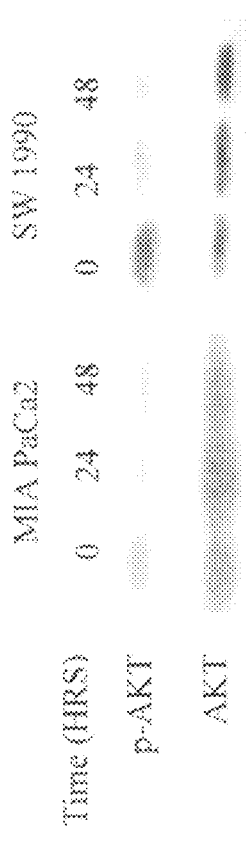
FIG. 3B is a blot series showing MIA PaCa2 and SW1990 cells treated with δ-tocotrienol (20 μM) for 24 and 48 hours. Cell lysates were run by SDS-PAGE and immunoblotted for p-AKT and AKT (Cell Signaling). The blots show a decrease in p-AKT protein levels, but not AKT at 24 and 48 hours.

HPDE 6C7 cells were resistant to the inhibitory effects of δ-tocotrienol. MIA PaCa2 and SW1990 cells were then treated with δ-tocotrienol (20 µM) for 24 and 48 hours. Cell lysates were run by SDS-PAGE and immunoblotted for p-AKT and AKT (Cell Signaling). FIG. 3B demonstrates a decrease in p-AKT protein levels, but not AKT at 24 and 48 hours. Taken together, the inhibition of downstream effectors of oncogenic Ras signaling by δ-tocotrienol without an affect on Ras protein levels may indicate a negative regulatory role of δ-tocotrienol on the function of oncogenic Ras.

Figure 4A:
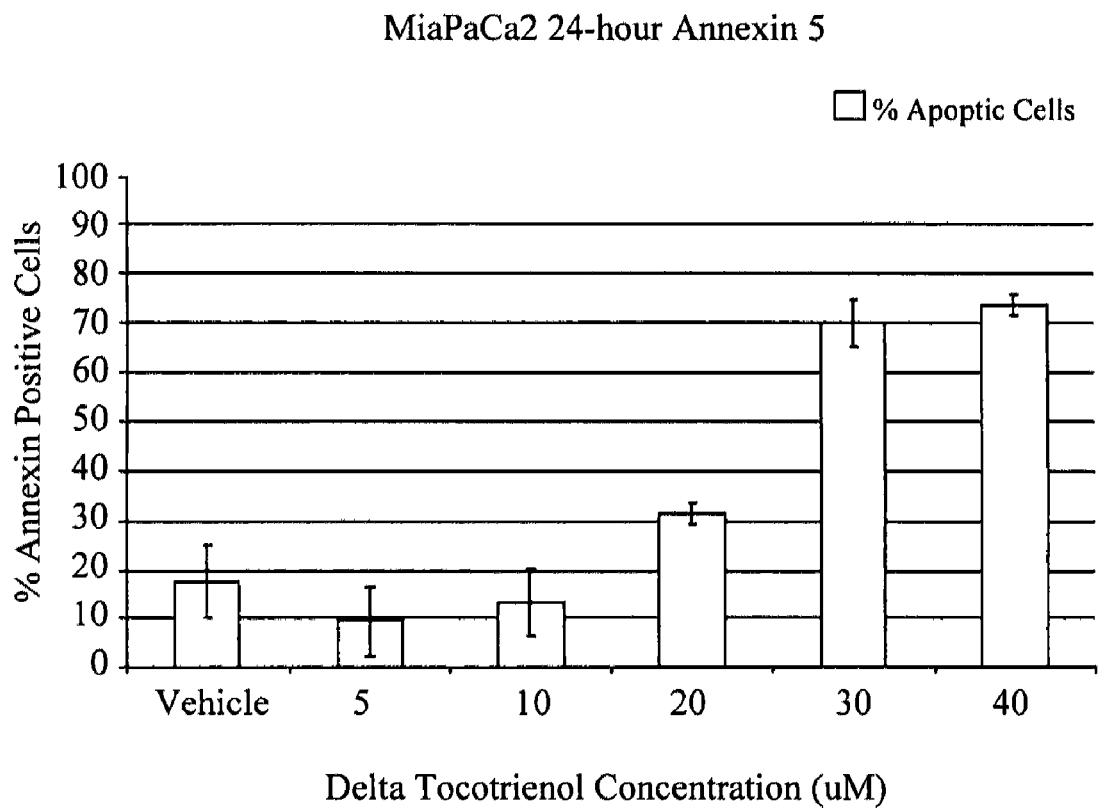
FIG. 4A is a graph showing activation of the caspase cascade as evidenced by cleavage of Caspase 8, Caspase 3, and Parp in a time dependent manner.
Figure 4B:
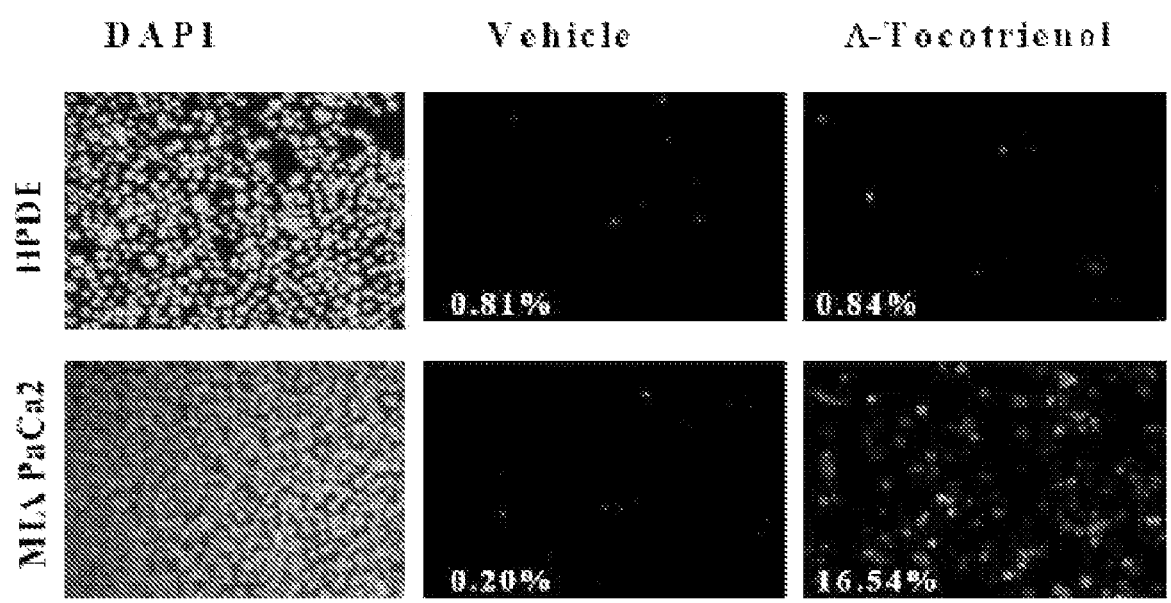
FIG. 4B is a series of images showing activation of the caspase cascade as evidenced by cleavage of Caspase 8, Caspase 3, and Parp in a time dependent manner.
Figure 4C:
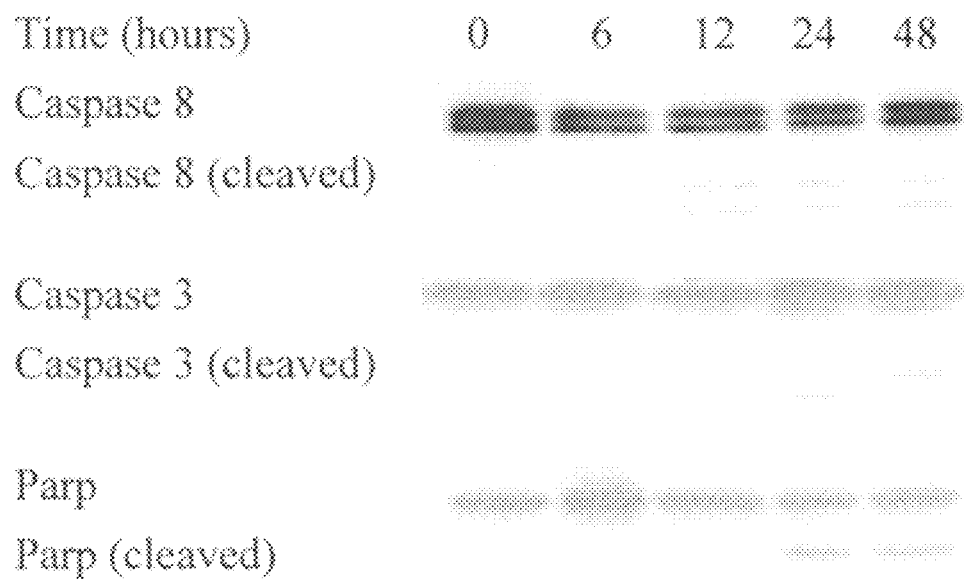
FIG. 4C is a series of blots showing activation of the caspase cascade as evidenced by cleavage of Caspase 8, Caspase 3, and Parp in a time dependent manner.
Figure 4D:
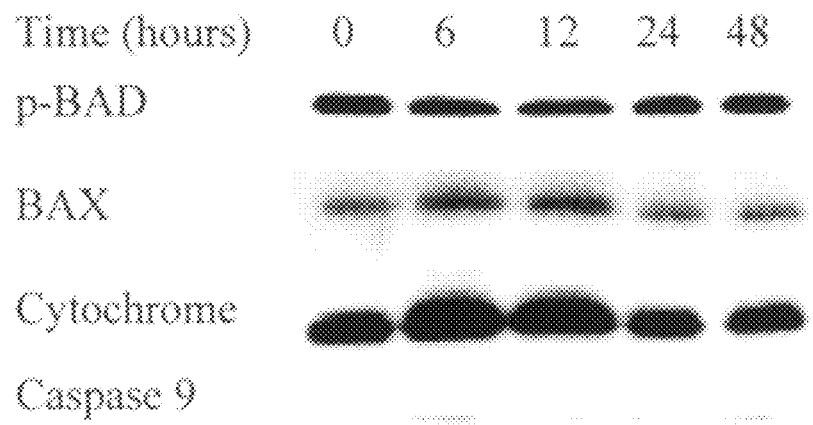
FIG. 4D is a series of blots showing activation of the caspase cascade as evidenced by cleavage of Caspase 8, Caspase 3, and Parp in a time dependent manner.

In addition to its chemopreventive effects, δ-Tocotrienol induces apoptosis in pancreatic cancer. MIA PaCa2 cells were treated with either δ-tocotrienol or vehicle for 24 hours. Cells were collected and stained with Annexin V-FITC and analyzed by flow cytometry for apoptosis. FIG. 4A shows a dose dependent induction of early apoptosis in MIA PaCa2 cells treated with δ-tocotrienol. δ-tocotrienol selectively induced apoptosis in pancreatic cancer cells MIA PaCa2 cells and HPDE 6C7 cells were treated with vehicle or δ-tocotrienol (20 µM) for 24 hours. Cells were harvested and stained for TUNEL. FIG. 4B shows significant staining of MIA PaCa2 cells treated with δ-tocotrienol for TUNEL compared to vehicle or treated HPDE 6C7 cells. This finding suggests selective induction of apoptosis in pancreatic cancer cells. Next, cell lysates were prepared from MIA PaCa2 cells treated with δ-tocotrienol (20 µM) at progressive time intervals as described above. Proteins from lysates were run by SDS PAGE and immunoblotted for biomarkers of apoptosis. FIG. 4C shows activation of the caspase cascade as evidenced by cleavage of Caspase 8, Caspase 3, and Parp in a time dependent manner. Interestingly, MIA PaCa2 cells treated with δ-tocotrienol had no significant effect on mitochondrial pro-apoptotic proteins as shown by a lack of cytochrome C release or cleavage of Caspase 9. Taken together, these data show that induction of apoptosis by δ-tocotrienol in pancreatic cancer cells occurs through activation of the extrinsic apoptotic pathway.

δ-Tocotrienol also Suppresses Pancreatic Cancer Growth In Vivo.

Treatment of pancreatic cancer cell lines resulted in induction of apoptosis in vitro and in vivo. The apoptotic effect of delta-tocotrienol was selective for neoplastic cells because immortalized human pancreatic ductal epithelial cells were not sensitive to delta-tocotrienol. Treatment of pancreatic cancer cell lines resulted in activation of the caspase cascade of the extrinsic pathway of apoptosis induction as evidenced by cleavage of Caspase 8 and Caspase 3 but not caspase 9. Further evidence of the lack of mitochondrial mediated apoptosis in delta-tocotrienol induced apoptosis of pancreatic cancer cells was demonstrated by the lack of cytochrome C release and the absence of delta-tocotrienol modulation of mitochondrial associated proteins such as Bcl-2 and Bad.

Figure 5A:
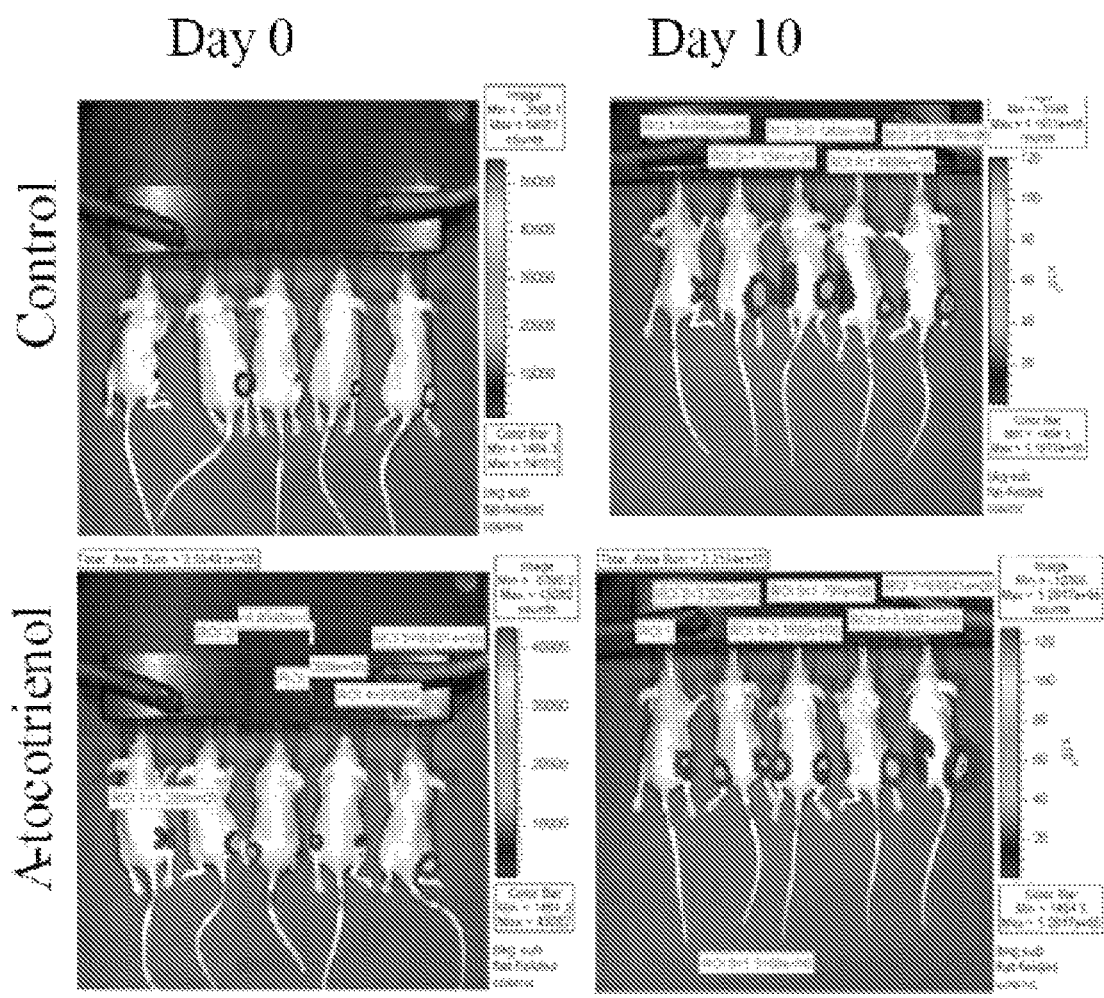
FIG. 5A shows representative luminescent measurements of control and δ-tocotrienol groups prior to treatment and at day 10. Rate of growth by day 10 of treatment is less in the tocotrienol treatment group. Stable transfectants of MIA PaCa2 cells with luciferase were injected subcutaneously into nude mice. Tumor volumes were measured every 2 days with calibers and the rate of growth was determined weekly by measuring tumor luminescence using the IVIS 100 Xenogen system. Tumors of similar volume (100-150 mm$^3$) and rate of growth based on luminescence were randomized to receive either vehicle or δ-tocotrienol (100 mg/kg/day) by gavage for 20 days.

Stable transfectants of MIA PaCa2 cells with luciferase were injected subcutaneously into nude mice. Tumor volumes were measured every 2 days with calibers and the rate of growth was determined weekly by measuring tumor luminescence using the IVIS 100 Xenogen system. Tumors of similar volume (100-150 mm$^3$) and rate of growth based on luminescence were randomized to receive either vehicle or δ-tocotrienol (100 mg/kg/day) by gavage for 20 days. FIG. 5A shows representative luminescent measurements of control and δ-tocotrienol groups prior to treatment and at day 10. Rate of growth by day 10 of treatment is less in the tocotrienol treatment group.

Figure 5B:
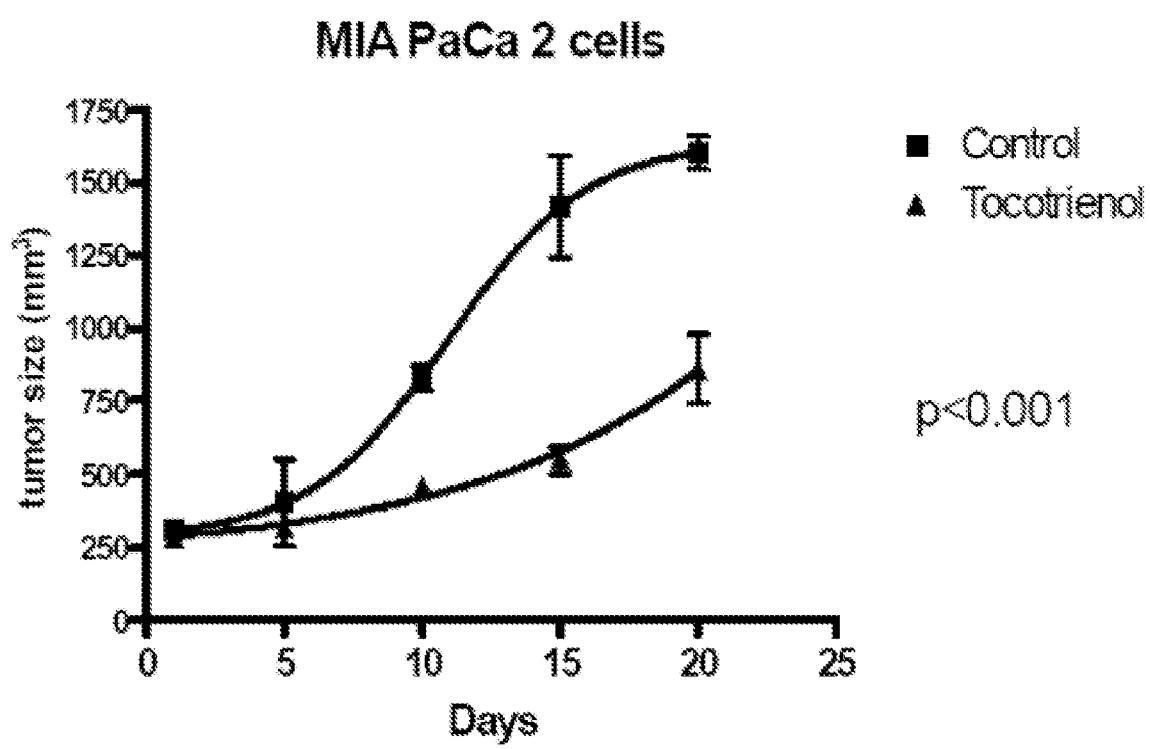
FIG. 5B is a graph showing significant reduction in tumor growth by 50% in xenografts treated with δ-tocotrienol compared to vehicle.
Figure 5C:
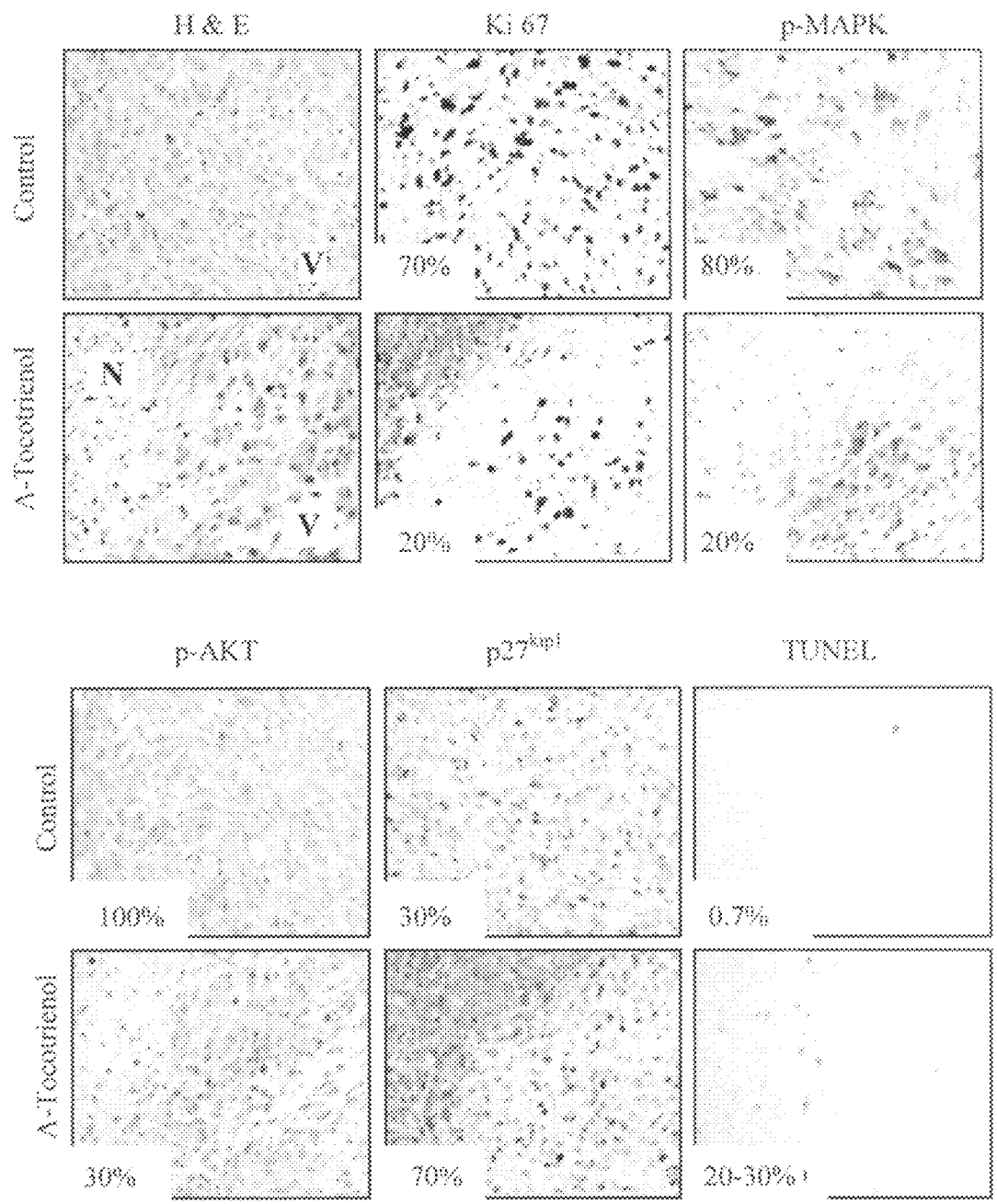
FIG. 5C is a series of immunohistochemical stains of the effects of δ-tocotrienol on oncogenic Ras signaling targets. Inhibition of proliferation is evidenced by a decrease in Ki67 and induction of apoptosis by TUNEL in tumors from mice treated with δ-tocotrienol as compared to tumors from the control group.

FIG. 5B shows significant reduction in tumor growth by 50% in xenografts treated with δ-tocotrienol compared to vehicle. Tumors were extracted on the last day of treatment and imbedded in paraffin. Immunohistochemical staining was performed to determine the effects of δ-tocotrienol on oncogenic Ras signaling targets. FIG. 5C shows inhibition of proliferation as evidenced by a decrease in Ki67 and induction of apoptosis by TUNEL in tumors from mice treated with δ-tocotrienol as compared to tumors from the control group. Furthermore, the biomarker proteins p-MAPK and p-AKT are decreased and p27$^{kip1}$ expression is increased in δ-tocotrienol treated tumors. These in vivo findings demonstrate reproducible alterations in cell signaling proteins shown in vitro, above.

EXAMPLE I

SW1990 pancreatic cancer cells (Panc-1) were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine. HPDE6-C7 cells were cultured in serum-free keratinocyte SFM media. All cells were maintained at 37° C. in a humidified incubator with 5% CO2.

Figure 6:
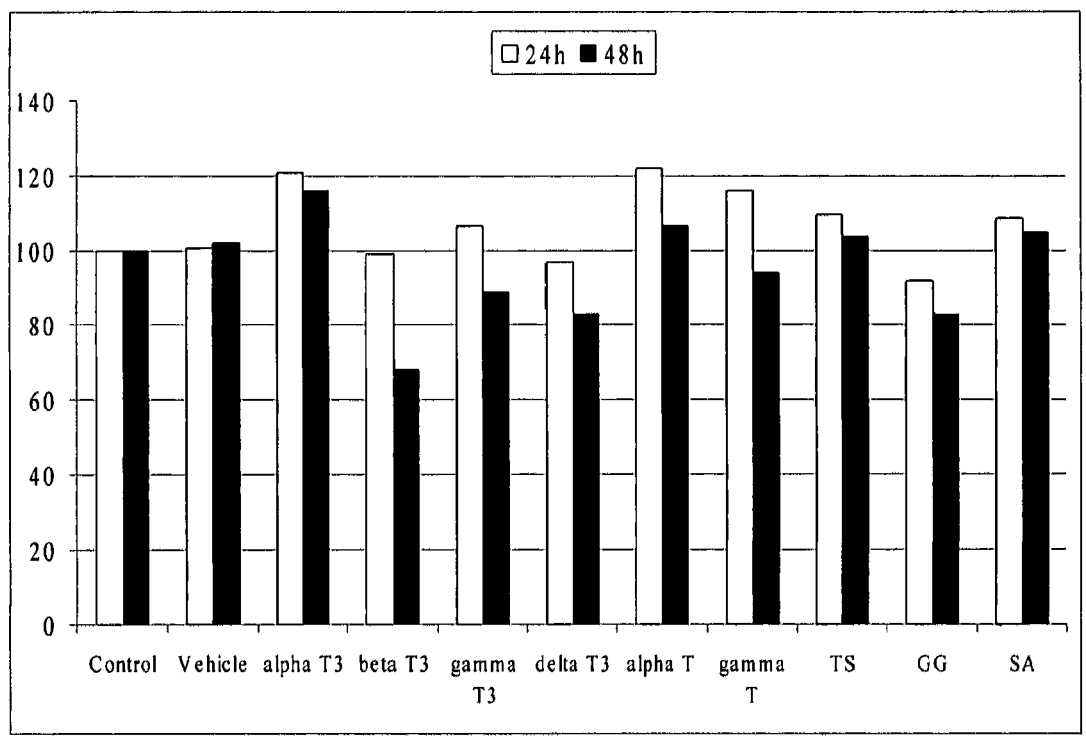
FIG. 6 is a graph of the MTS analysis of SW1990 pancreatic cancer cells (Panc-1), 24 and 48 hours, shown in Tables I-II.

Tables I (24 hours), II (48 hours) and III (72 hours) show the associated results. The columns of each table are the different treatments, comprising a single dose (50 µM) as follows: Control (no treatment), Vehicle (vehicle only, maybe a solvent), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). The numbers in the cells of each column are the output of the MTS assay; with the exception of the last column which represents the average of the replicates, divided by the average of the control value (control is always 100). Each column represents 9 replicates. FIG. 6 illustrates the results for the 24 hour and 48 hour trials.

TABLE I

|  | Panc-1 (24 hours) | | | | | | | | | % |
| --- | --- | --- | --- | --- | --- | --- | --- | --- | --- | --- |
| Control | 0.167 | 0.156 | 0.151 | 0.161 | 0.142 | 0.147 | 0.142 | 0.109 | 0.147 | 100 |
| Vehicle | 0.15 | 0.146 | 0.147 | 0.14 | 0.155 | 0.151 | 0.164 | 0.138 | 0.149 | 101 |
| T3 alpha | 0.168 | 0.183 | 0.175 | 0.148 | 0.195 | 0.176 | 0.206 | 0.172 | 0.178 | 121 |
| T3 beta | 0.164 | 0.168 | 0.167 | 0.123 | 0.138 | 0.143 | 0.126 | 0.134 | 0.145 | 99 |
| T3 gamma | 0.169 | 0.161 | 0.163 | 0.143 | 0.15 | 0.158 | 0.159 | 0.151 | 0.157 | 107 |
| T3 delta | 0.158 | 0.149 | 0.157 | 0.126 | 0.147 | 0.135 | 0.13 | 0.142 | 0.143 | 97 |
| T alpha | 0.188 | 0.183 | 0.189 | 0.166 | 0.183 | 0.181 | 0.186 | 0.16 | 0.180 | 122 |
| T gamma | 0.175 | 0.165 | 0.167 | 0.154 | 0.198 | 0.168 | 0.178 | 0.16 | 0.171 | 116 |
| TS | 0.155 | 0.168 | 0.164 | 0.158 | 0.155 | 0.163 | 0.165 | 0.167 | 0.162 | 110 |

TABLE I-continued

|  | Panc-1 (24 hours) |  |  |  |  |  |  |  |  | % |
|---|---|---|---|---|---|---|---|---|---|---|
| GG | 0.158 | 0.133 | 0.133 | 0.137 | 0.131 | 0.14 | 0.132 | 0.121 | 0.136 | 92 |
| SA | 0.146 | 0.154 | 0.15 | 0.152 | 0.172 | 0.165 | 0.179 | 0.165 | 0.160 | 109 |

TABLE II

|  | Panc-1 (48 hours) |  |  |  |  |  |  |  |  | % |
|---|---|---|---|---|---|---|---|---|---|---|
| Control | 0.161 | 0.156 | 0.16 | 0.137 | 0.148 | 0.152 | 0.15 | 0.152 | 0.152 | 100 |
| Vehicle | 0.169 | 0.152 | 0.16 | 0.146 | 0.143 | 0.149 | 0.16 | 0.162 | 0.154 | 102 |
| T3 alpha | 0.168 | 0.162 | 0.16 | 0.146 | 0.175 | 0.205 | 0.2 | 0.187 | 0.175 | 116 |
| T3 beta | 0.108 | 0.093 | 0.09 | 0.104 | 0.109 | 0.117 | 0.1 | 0.102 | 0.104 | 68 |
| T3 gamma | 0.114 | 0.125 | 0.13 | 0.123 | 0.137 | 0.137 | 0.16 | 0.16 | 0.135 | 89 |
| T3 delta | 0.131 | 0.133 | 0.12 | 0.12 | 0.126 | 0.119 | 0.12 | 0.142 | 0.127 | 83 |
| T alpha | 0.172 | 0.17 | 0.16 | 0.154 | 0.154 | 0.167 | 0.18 | 0.146 | 0.163 | 107 |
| T gamma | 0.131 | 0.133 | 0.14 | 0.141 | 0.142 | 0.122 | 0.16 | 0.164 | 0.142 | 94 |
| TS | 0.122 | 0.166 | 0.16 | 0.135 | 0.148 | 0.174 | 0.18 | 0.173 | 0.157 | 104 |
| GG | 0.078 | 0.129 | 0.13 | 0.128 | 0.133 | 0.118 | 0.14 | 0.144 | 0.125 | 83 |
| SA | 0.122 | 0.149 | 0.17 | 0.138 | 0.177 | 0.159 | 0.18 | 0.178 | 0.159 | 105 |

TABLE III

|  | Panc-1 (72 hours) |  |  |  |  |  |  |  |  | % |
|---|---|---|---|---|---|---|---|---|---|---|
| Control | 0.464 | 0.511 | 0.45 | 0.421 | 0.428 | 0.42 | 0.43 | 0.433 | 0.444 | 100 |
| Vehicle | 0.409 | 0.358 | 0.35 | 0.321 | 0.345 | 0.304 | 0.32 | 0.336 | 0.344 | 77 |
| T3 alpha | 0.279 | 0.282 | 0.29 | 0.238 | 0.302 | 0.279 | 0.25 | 0.254 | 0.273 | 61 |
| T3 beta | 0.349 | 0.316 | 0.33 | 0.298 | 0.323 | 0.287 | 0.28 | 0.275 | 0.307 | 69 |
| T3 gamma | 0.776 | 0.744 | 0.88 | 0.734 | 0.812 | 0.817 | 0.77 | 0.759 | 0.786 | 177 |
| T3 delta | 0.667 | 0.615 | 0.61 | 0.587 | 0.582 | 0.491 | 0.52 | 0.604 | 0.584 | 132 |
| T alpha | 0.523 | 0.478 | 0.46 | 0.453 | 0.443 | 0.456 | 0.38 | 0.451 | 0.456 | 103 |
| T gamma | 0.5 | 0.497 | 0.46 | 0.505 | 0.515 | 0.469 | 0.43 | 0.451 | 0.478 | 108 |
| TS | 0.998 | 0.962 | 1.02 | 0.887 | 0.936 | 0.897 | 0.85 | 0.801 | 0.918 | 207 |
| GG | 0.784 | 0.713 | 0.76 | 0.734 | 0.682 | 0.665 | 0.65 | 0.627 | 0.702 | 158 |
| SA | 0.596 | 0.547 | 0.57 | 0.515 | 0.544 | 0.44 | 0.4 | 0.427 | 0.504 | 113 |

EXAMPLE II

MiaPaCa-2 cells were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine. HPDE6-C7 cells were cultured in serum-free keratinocyte SFM media. All cells were maintained at 37° C. in a humidified incubator with 5% CO2.

Figure 7:
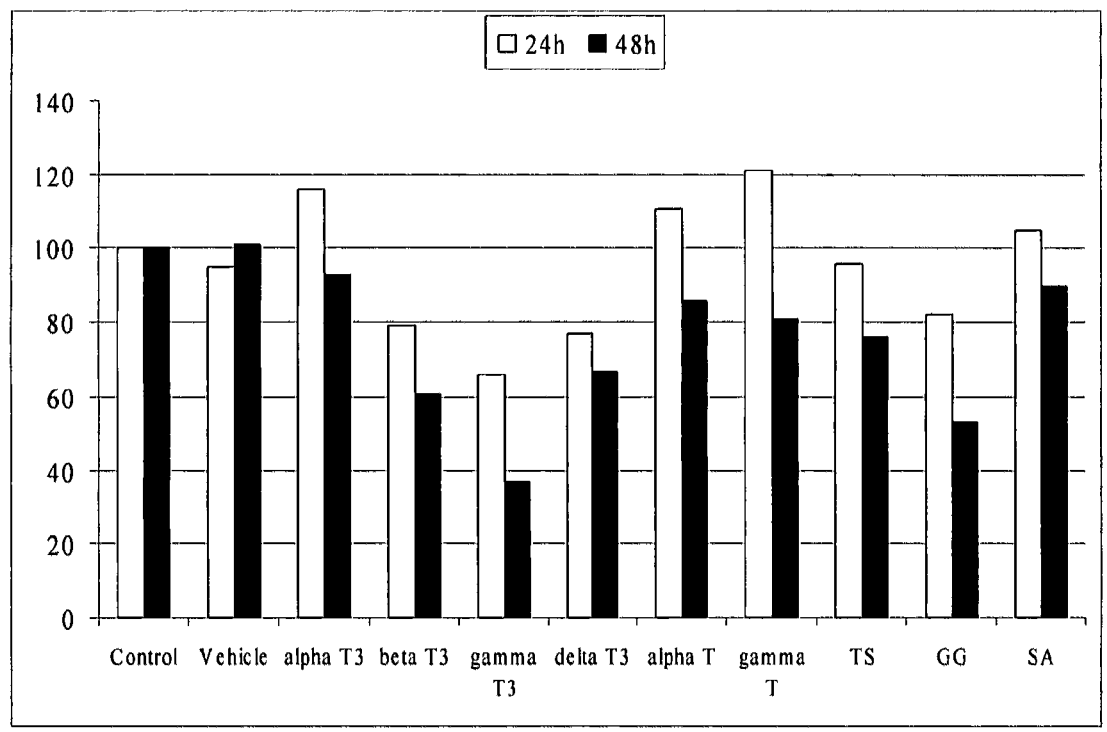
FIG. 7 is a graph of the MTS analysis of MiaPaCa2 pancreatic cancer cells, 24 and 48 hours, shown in Tables IV-V.

Tables IV (24 hours), V (48 hours) and VI (72 hours) show the associated results. The columns of each table are the different treatments, comprising a single dose (50 μM) as follows: Control (no treatment), Vehicle (vehicle only, maybe a solvent), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). The numbers in the cells of each column are the output of the MTS assay; with the exception of the last column which represents the average of the replicates, divided by the average of the control value (control is always 100). Each column represents 9 replicates. FIG. 7 illustrates the results for the 24 hour and 48 hour trials.

TABLE IV

|  | MiaPaCa-2 (24 hours) |  |  |  |  |  |  |  |  | % |
|---|---|---|---|---|---|---|---|---|---|---|
| Control | 0.225 | 0.226 | 0.223 | 0.216 | 0.239 | 0.204 | 0.226 | 0.219 | 0.222 | 100 |
| Vehicle | 0.266 | 0.238 | 0.225 | 0.192 | 0.183 | 0.2 | 0.189 | 0.198 | 0.211 | 95 |
| T3 alpha | 0.274 | 0.296 | 0.293 | 0.216 | 0.245 | 0.258 | 0.243 | 0.239 | 0.258 | 116 |
| T3 beta | 0.17 | 0.179 | 0.184 | 0.152 | 0.172 | 0.182 | 0.179 | 0.19 | 0.176 | 79 |
| T3 gamma | 0.133 | 0.135 | 0.141 | 0.127 | 0.142 | 0.166 | 0.171 | 0.162 | 0.147 | 66 |
| T3 delta | 0.174 | 0.159 | 0.171 | 0.139 | 0.185 | 0.187 | 0.18 | 0.167 | 0.170 | 77 |
| T alpha | 0.249 | 0.25 | 0.253 | 0.207 | 0.253 | 0.238 | 0.27 | 0.254 | 0.247 | 111 |
| T gamma | 0.273 | 0.261 | 0.268 | 0.219 | 0.264 | 0.31 | 0.295 | 0.263 | 0.269 | 121 |
| TS | 0.24 | 0.211 | 0.226 | 0.172 | 0.221 | 0.201 | 0.214 | 0.228 | 0.214 | 96 |
| GG | 0.186 | 0.166 | 0.175 | 0.18 | 0.196 | 0.199 | 0.184 | 0.178 | 0.183 | 82 |
| SA | 0.24 | 0.248 | 0.25 | 0.245 | 0.236 | 0.219 | 0.214 | 0.204 | 0.232 | 105 |

TABLE V

| | MiaPaCa-2 (48 hours) | | | | | | | | | % |
|---|---|---|---|---|---|---|---|---|---|---|
| Control | 0.364 | 0.354 | 0.321 | 0.362 | 0.416 | 0.296 | 0.382 | 0.397 | 0.362 | 100 |
| Vehicle | 0.374 | 0.357 | 0.356 | 0.331 | 0.382 | 0.389 | 0.396 | 0.335 | 0.365 | 101 |
| T3 alpha | 0.336 | 0.325 | 0.343 | 0.327 | 0.39 | 0.376 | 0.322 | 0.286 | 0.338 | 93 |
| T3 beta | 0.193 | 0.137 | 0.227 | 0.223 | 0.231 | 0.272 | 0.225 | 0.27 | 0.222 | 61 |
| T3 gamma | 0.095 | 0.116 | 0.111 | 0.128 | 0.159 | 0.147 | 0.167 | 0.152 | 0.134 | 37 |
| T3 delta | 0.229 | 0.22 | 0.218 | 0.232 | 0.294 | 0.272 | 0.221 | 0.243 | 0.241 | 67 |
| T alpha | 0.308 | 0.313 | 0.342 | 0.269 | 0.352 | 0.277 | 0.305 | 0.339 | 0.313 | 86 |
| T gamma | 0.329 | 0.265 | 0.304 | 0.25 | 0.289 | 0.341 | 0.301 | 0.279 | 0.295 | 81 |
| TS | 0.257 | 0.254 | 0.262 | 0.237 | 0.258 | 0.275 | 0.32 | 0.337 | 0.275 | 76 |
| GG | 0.154 | 0.194 | 0.181 | 0.198 | 0.236 | 0.198 | 0.193 | 0.192 | 0.193 | 53 |
| SA | 0.334 | 0.335 | 0.333 | 0.304 | 0.32 | 0.294 | 0.352 | 0.348 | 0.328 | 90 |

TABLE VI

| | MiaPaCa-2 (72 hours) | | | | | | | | | % |
|---|---|---|---|---|---|---|---|---|---|---|
| Control | 0.464 | 0.511 | 0.447 | 0.421 | 0.428 | 0.42 | 0.43 | 0.433 | 0.444 | 100 |
| Vehicle | 0.409 | 0.358 | 0.353 | 0.321 | 0.345 | 0.304 | 0.322 | 0.336 | 0.344 | 77 |
| T3 alpha | 0.279 | 0.282 | 0.294 | 0.238 | 0.302 | 0.279 | 0.254 | 0.254 | 0.273 | 61 |
| T3 beta | 0.349 | 0.316 | 0.328 | 0.298 | 0.323 | 0.287 | 0.281 | 0.275 | 0.307 | 69 |
| T3 gamma | 0.776 | 0.744 | 0.876 | 0.734 | 0.812 | 0.817 | 0.773 | 0.759 | 0.786 | 177 |
| T3 delta | 0.667 | 0.615 | 0.605 | 0.587 | 0.582 | 0.491 | 0.524 | 0.604 | 0.584 | 132 |
| T alpha | 0.523 | 0.478 | 0.464 | 0.453 | 0.443 | 0.456 | 0.383 | 0.451 | 0.456 | 103 |
| T gamma | 0.5 | 0.497 | 0.46 | 0.505 | 0.515 | 0.469 | 0.429 | 0.451 | 0.478 | 108 |
| TS | 0.998 | 0.962 | 1.016 | 0.887 | 0.936 | 0.897 | 0.85 | 0.801 | 0.918 | 207 |
| GG | 0.784 | 0.713 | 0.757 | 0.734 | 0.682 | 0.665 | 0.65 | 0.627 | 0.702 | 158 |
| SA | 0.596 | 0.547 | 0.566 | 0.515 | 0.544 | 0.44 | 0.397 | 0.427 | 0.504 | 114 |

EXAMPLE III

MiaPaCa-2 cells were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine. HPDE6-C7 cells were cultured in serum-free keratinocyte SFM media. All cells were maintained at 37° C. in a humidified incubator with 5% CO2.

Table VII (48 hours) and Table VIII (5 Days) show the associated results. The columns of each table are the different treatments, comprising a single dose (50 μM) as follows: Control (no treatment), Vehicle (vehicle only, maybe a solvent), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). Each column represents 7 replicates with one blank. The numbers in the cells of each column are the output of the MTT assay; with the exception of the bottom three rows which represent, respectively: the average of the replicates, the average of the replicates including the blank, and the average of the replicates divided by the average of the control value (control is always 100).

TABLE VII

| | MiaPaCa-2 (5 Days) | | | | | | | Average | Average-Blank | % |
|---|---|---|---|---|---|---|---|---|---|---|
| Blank | 0.047 | 0.048 | 0.048 | 0.045 | 0.049 | 0.041 | 0.046 | | | |
| Control | 0.384 | 0.372 | 0.341 | 0.333 | 0.382 | 0.345 | 0.332 | 0.356 | 0.310 | 100 |
| Vehicle | 0.342 | 0.315 | 0.309 | 0.342 | 0.347 | 0.321 | 0.306 | 0.326 | 0.280 | 90 |
| T3 alpha | 0.349 | 0.341 | 0.356 | 0.329 | 0.349 | 0.316 | 0.323 | 0.338 | 0.292 | 94 |
| T3 beta | 0.272 | 0.235 | 0.233 | 0.226 | 0.252 | 0.219 | 0.239 | 0.239 | 0.193 | 62 |
| T3 gamma | 0.185 | 0.181 | 0.156 | 0.183 | 0.21 | 0.141 | 0.137 | 0.170 | 0.124 | 40 |
| T3 delta | 0.276 | 0.284 | 0.262 | 0.239 | 0.275 | 0.239 | 0.269 | 0.263 | 0.217 | 70 |
| T alpha | 0.365 | 0.352 | 0.339 | 0.338 | 0.35 | 0.297 | 0.35 | 0.342 | 0.296 | 95 |
| T gamma | 0.35 | 0.323 | 0.312 | 0.36 | 0.348 | 0.328 | 0.348 | 0.338 | 0.292 | 94 |
| TS | 0.215 | 0.184 | 0.2 | 0.187 | 0.194 | 0.19 | 0.185 | 0.194 | 0.148 | 48 |
| GG | 0.329 | 0.339 | 0.321 | 0.328 | 0.342 | 0.317 | 0.341 | 0.331 | 0.285 | 92 |
| SA | 0.276 | 0.269 | 0.268 | 0.276 | 0.3 | 0.262 | 0.266 | 0.274 | 0.228 | 74 |

TABLE VIII

| | MiaPaCa-2 (5 Days) | | | | | | | Average | Average-Blank | % |
|---|---|---|---|---|---|---|---|---|---|---|
| Blank | 0.051 | 0.052 | 0.052 | 0.052 | 0.052 | 0.053 | 0.052 | | | |
| Control | 1.803 | 1.86 | 1.75 | 1.832 | 2.241 | 1.751 | 1.79 | 1.861 | 1.809 | 100 |
| Vehicle | 1.733 | 1.661 | 1.594 | 1.754 | 2.161 | 1.703 | 1.68 | 1.755 | 1.703 | 94 |
| T3 alpha | 1.497 | 1.573 | 1.569 | 1.55 | 1.811 | 1.589 | 1.47 | 1.580 | 1.528 | 84 |
| T3 beta | 0.97 | 0.781 | 0.977 | 1.154 | 1.408 | 0.944 | 0.891 | 1.018 | 0.966 | 53 |
| T3 gamma | 0.088 | 0.084 | 0.098 | 0.089 | 0.12 | 0.084 | 0.092 | 0.094 | 0.042 | 2 |
| T3 delta | 1.344 | 1.314 | 1.27 | 1.337 | 1.579 | 1.308 | 1.341 | 1.356 | 1.304 | 72 |
| T alpha | 1.56 | 1.647 | 1.59 | 1.619 | 2.059 | 1.526 | 1.588 | 1.656 | 1.604 | 89 |
| T gamma | 1.52 | 1.516 | 1.547 | 1.625 | 1.917 | 1.568 | 1.635 | 1.618 | 1.566 | 87 |
| TS | 0.732 | 0.776 | 0.786 | 0.714 | 0.939 | 0.859 | 0.968 | 0.825 | 0.773 | 43 |
| GG | 1.738 | 1.608 | 1.577 | 1.744 | 2.134 | 1.606 | 1.711 | 1.731 | 1.679 | 93 |
| SA | 1.36 | 1.346 | 1.488 | 1.609 | 1.84 | 1.412 | 1.408 | 1.495 | 1.443 | 80 |

EXAMPLE IV

BXPC3 cells were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine. HPDE6-C7 cells were cultured in serum-free keratinocyte SFM media. All cells were maintained at 37° C. in a humidified incubator with 5% CO2.

Table IX (48 hours) and Table X (5 Days) show the associated results. The columns of each table are the different treatments, comprising a single dose (50 µM) as follows: Control (no treatment), Vehicle (vehicle only, maybe a solvent), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). Each column represents 7 replicates with one blank. The numbers in the cells of each column are the output of the MTT assay; with the exception of the bottom three rows which represent, respectively: the average of the replicates, the average of the replicates including the blank, and the average of the replicates divided by the average of the control value (control is always 100).

TABLE IX

| | BXCPC3 (48 Hours) | | | | | | | Average | Average-Blank | % |
|---|---|---|---|---|---|---|---|---|---|---|
| Blank | 0.048 | 0.047 | 0.049 | 0.051 | 0.05 | 0.047 | 0.049 | | | |
| Control | 0.279 | 0.282 | 0.28 | 0.273 | 0.267 | 0.287 | 0.274 | 0.28 | 0.277 | 0.228 | 100 |
| Vehicle | 0.255 | 0.274 | 0.276 | 0.256 | 0.295 | 0.292 | 0.285 | 0.276 | 0.227 | 100 |
| T3 alpha | 0.279 | 0.275 | 0.295 | 0.301 | 0.3 | 0.273 | 0.275 | 0.285 | 0.236 | 104 |
| T3 beta | 0.263 | 0.261 | 0.27 | 0.254 | 0.278 | 0.255 | 0.274 | 0.265 | 0.216 | 95 |
| T3 gamma | 0.259 | 0.257 | 0.289 | 0.279 | 0.268 | 0.292 | 0.283 | 0.275 | 0.226 | 99 |
| T3 delta | 0.26 | 0.255 | 0.24 | 0.263 | 0.271 | 0.277 | 0.288 | 0.265 | 0.216 | 95 |
| T alpha | 0.333 | 0.328 | 0.352 | 0.296 | 0.3 | 0.341 | 0.312 | 0.323 | 0.274 | 120 |
| T gamma | 0.32 | 0.356 | 0.335 | 0.304 | 0.277 | 0.28 | 0.306 | 0.311 | 0.262 | 115 |
| TS | 0.271 | 0.274 | 0.296 | 0.271 | 0.282 | 0.274 | 0.277 | 0.278 | 0.229 | 100 |
| GG | 0.308 | 0.272 | 0.299 | 0.291 | 0.299 | 0.3 | 0.294 | 0.295 | 0.246 | 108 |
| SA | 0.273 | 0.28 | 0.271 | 0.271 | 0.254 | 0.263 | 0.255 | 0.267 | 0.218 | 95 |

TABLE X

| | BXPC3 (5 Days) | | | | | | | Average | Average-Blank | % |
|---|---|---|---|---|---|---|---|---|---|---|
| Blank | 0.052 | 0.054 | 0.056 | 0.055 | 0.055 | 0.059 | 0.055 | | | |
| Control | 0.626 | 0.613 | 0.62 | 0.618 | 0.67 | 0.626 | 0.642 | 0.631 | 0.576 | 100 |
| Vehicle | 0.641 | 0.644 | 0.647 | 0.653 | 0.669 | 0.659 | 0.648 | 0.652 | 0.597 | 104 |
| T3 alpha | 0.584 | 0.637 | 0.594 | 0.63 | 0.62 | 0.61 | 0.618 | 0.613 | 0.558 | 97 |
| T3 beta | 0.468 | 0.512 | 0.495 | 0.481 | 0.457 | 0.483 | 0.411 | 0.472 | 0.417 | 72 |
| T3 gamma | 0.418 | 0.446 | 0.446 | 0.457 | 0.428 | 0.412 | 0.42 | 0.432 | 0.377 | 66 |
| T3 delta | 0.485 | 0.49 | 0.522 | 0.539 | 0.551 | 0.523 | 0.527 | 0.520 | 0.465 | 81 |
| T alpha | 0.657 | 0.642 | 0.666 | 0.659 | 0.705 | 0.66 | 0.672 | 0.666 | 0.611 | 106 |
| T gamma | 0.628 | 0.66 | 0.653 | 0.649 | 0.682 | 0.615 | 0.661 | 0.650 | 0.595 | 103 |
| TS | 0.192 | 0.127 | 0.142 | 0.162 | 0.116 | 0.129 | 0.199 | 0.152 | 0.097 | 17 |
| GG | 0.621 | 0.655 | 0.672 | 0.663 | 0.657 | 0.724 | 0.66 | 0.665 | 0.610 | 106 |
| SA | 0.456 | 0.471 | 0.497 | 0.487 | 0.493 | 0.48 | 0.494 | 0.483 | 0.428 | 74 |

Figure 8A:
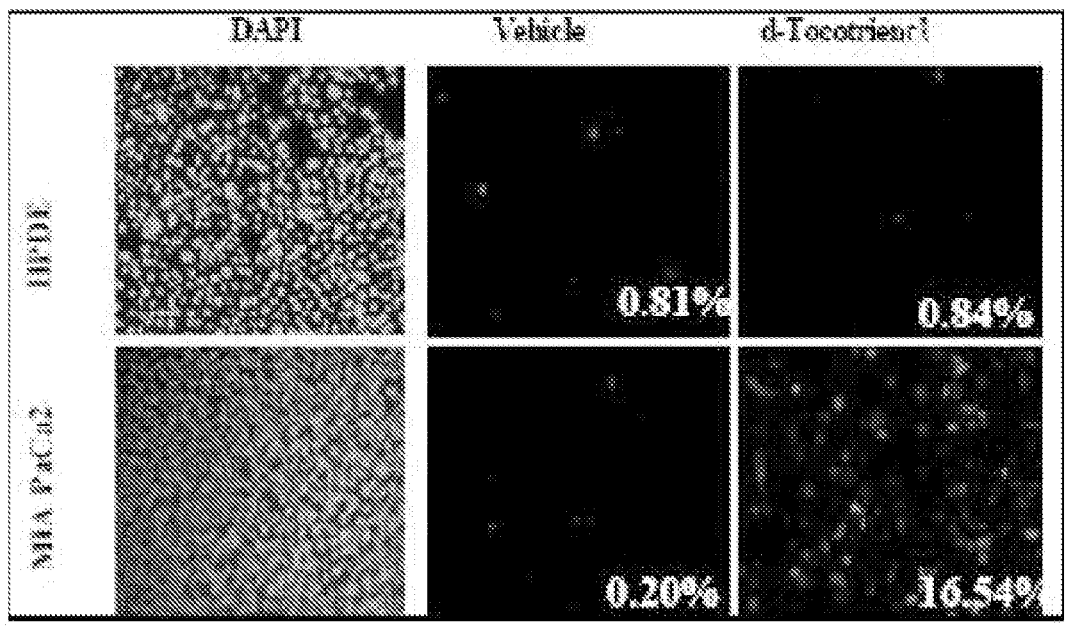
FIG. 8A is a series of images showing a significant increase in apoptotic cells in MIAPaCa2 treated with δ-tocotrienol compared to vehicle or treated HPDE 6C7 cells.
Figure 8B:
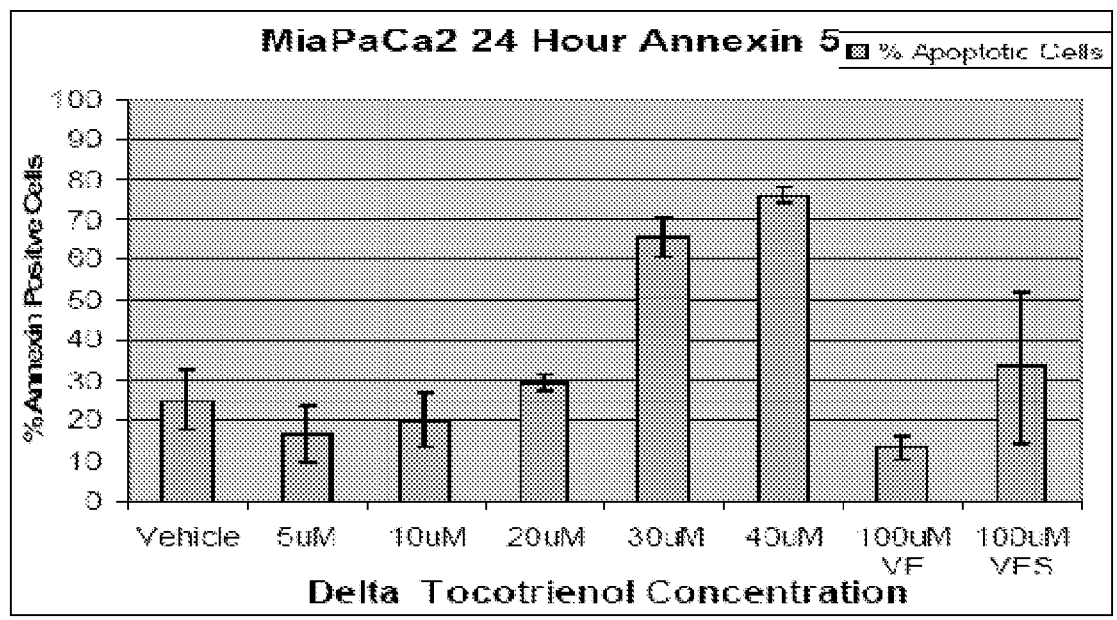
FIG. 8B is a graph wherein MIA PaCa-2 pancreatic cancer cells were treated with in varying concentrations of δ-tocotrienol or vehicle for 24 hours. Cells were collected and stained with Annexin V-FITC and analyzed by flow cytometry for apoptosis.
Figure 8C:
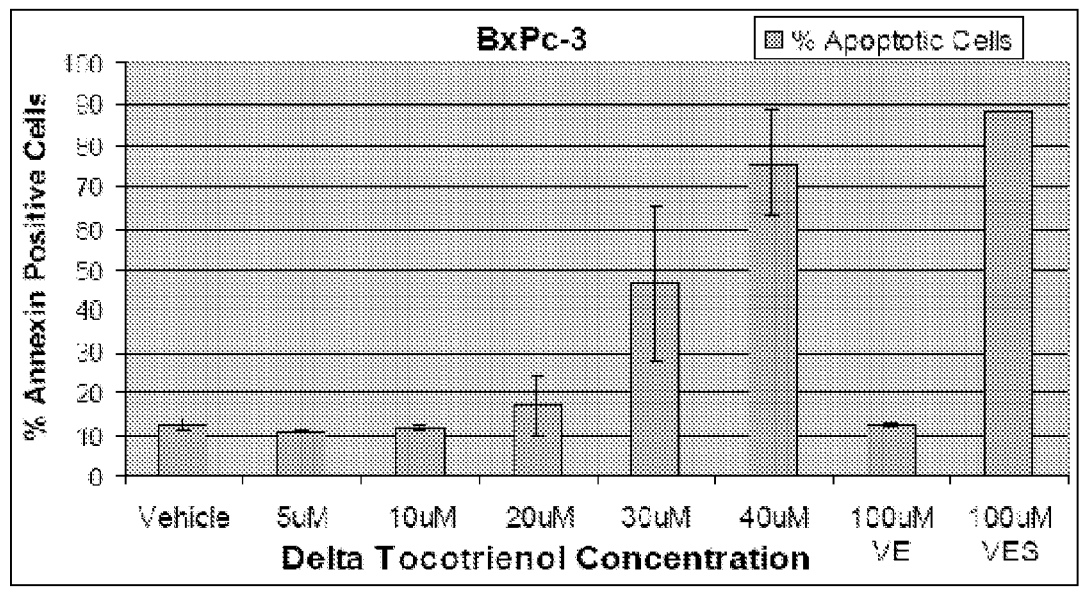
FIG. 8C is a graph wherein BXPC3 pancreatic cancer cells were treated with in varying concentrations of δ-tocotrienol or vehicle for 24 hours. Cells were collected and stained with Annexin V-FITC and analyzed by flow cytometry for apoptosis.
Figure 8D:
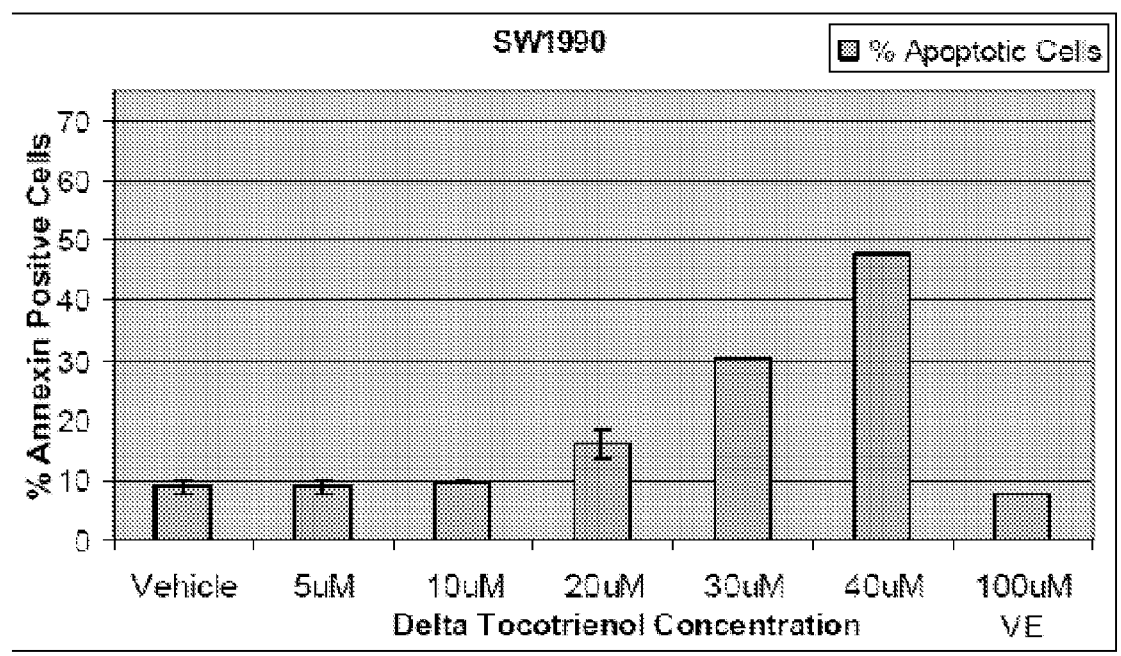
FIG. 8D is a graph wherein SW1990 pancreatic cancer cells were treated with in varying concentrations of δ-tocotrienol or vehicle for 24 hours. Cells were collected and stained with Annexin V-FITC and analyzed by flow cytometry for apoptosis.

FIG. 8A shows a significant increase in apoptotic cells in MIAPaCa2 treated with δ-tocotrienol compared to vehicle or treated HPDE 6C7 cells. FIGS. 8B-8D. MIA PaCa-2, BxPc-3, and SW1990 pancreatic cancer cells were also treated with in varying concentrations of δ-tocotrienol or vehicle for 24 hours. Cells were collected and stained with Annexin V-FITC and analyzed by flow cytometry for apoptosis. FIGS. 8B, 8C and 8D show a dose dependent induction of apoptosis in MIA PaCa-2 cells treated with δ-tocotrienol compared to vehicle.

Figure 9A:
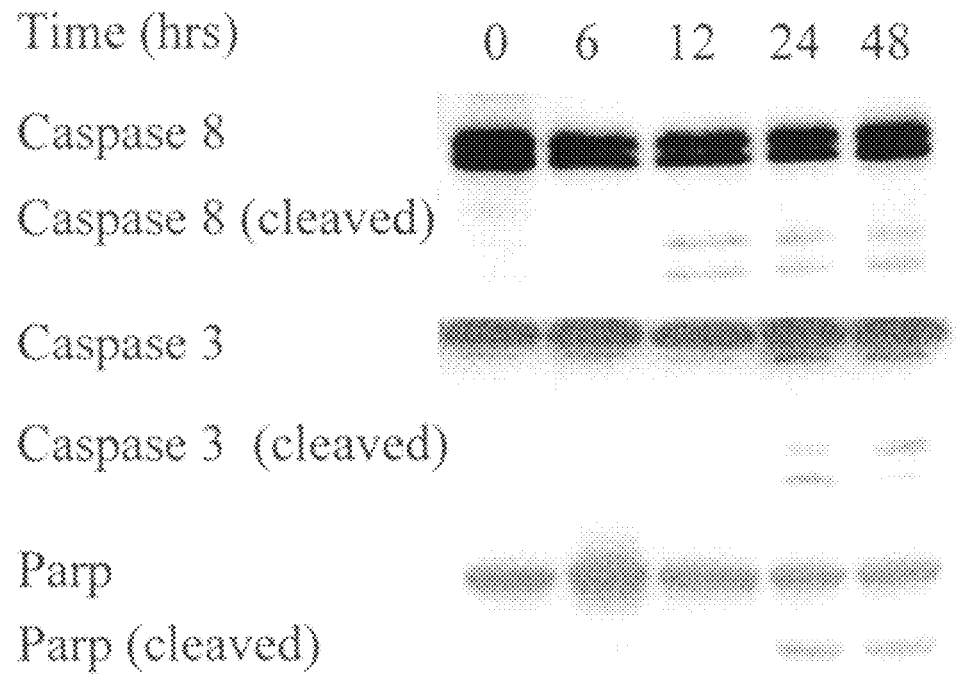
FIG. 9A shows activation of the caspase cascade as evidenced by cleavage of Caspase 8, Caspase 3, and PARP in a time dependent manner.
Figure 9B:
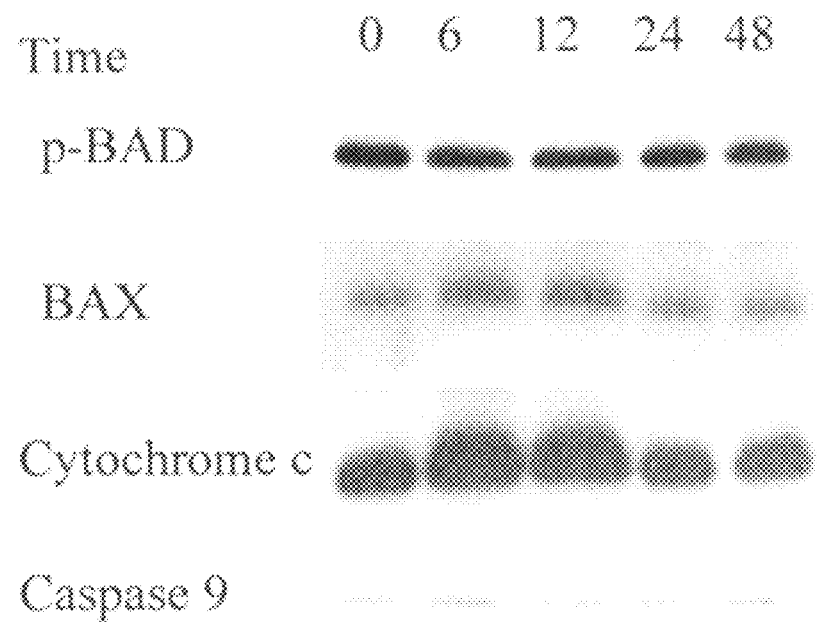
FIG. 9B shows MIA PaCa-2 cells treated with δ-tocotrienol had no significant effect on mitochondrial pro-apoptotic proteins as shown by a lack of cytochrome C release or cleavage of Caspase 9.
Figure 9C:
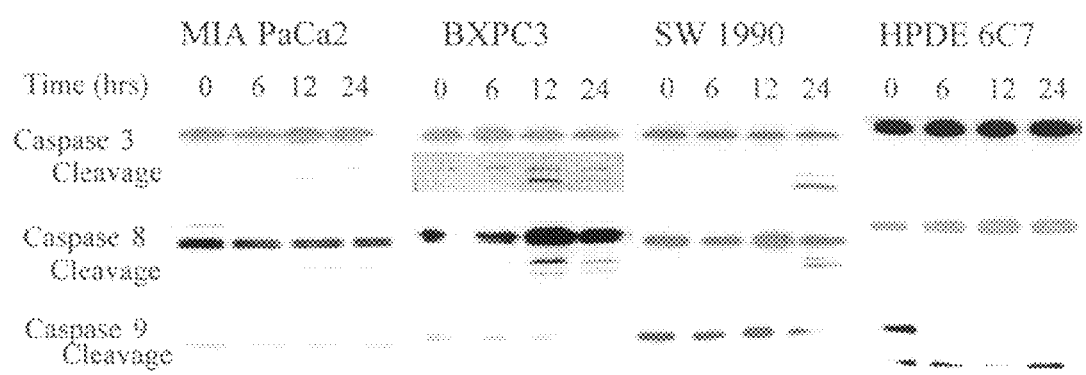
FIG. 9C shows selective caspase 8 and 3 cleavage in several pancreatic cancer cell lines but not in HPDE-6C7 cells, an immortalized pancreatic ductal epithelial cell line. Caspase 9 was not cleaved in the pancreatic cancer cells.
Figure 10:
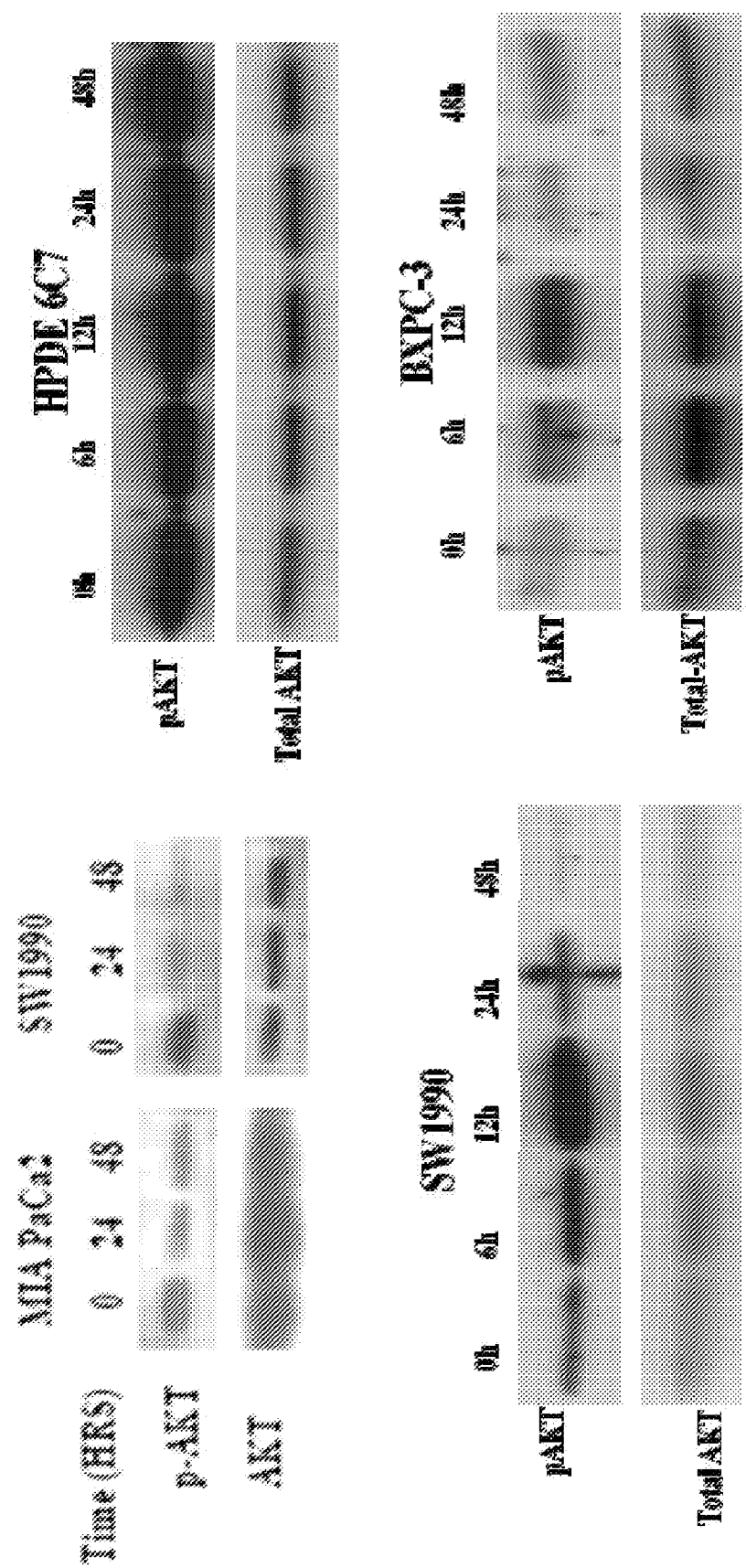
FIG. 10 shows a time-dependent decrease in phospho-AKT (but not total AKT) in the pancreatic cancer cell lines, but not in the HPDE cells.

FIG. 9A shows activation of the caspase cascade as evidenced by cleavage of Caspase 8, Caspase 3, and PARP in a time dependent manner. Interestingly, MIA PaCa-2 cells treated with δ-tocotrienol had no significant effect on mitochondrial pro-apoptotic proteins as shown by a lack of cytochrome C release or cleavage of Caspase 9 (9B). FIG. 9C shows selective caspase 8 and 3 cleavage in several pancreatic cancer cell lines but not in HPDE-6C7 cells, an immortalized pancreatic ductal epithelial cell line. Caspase 9 was not cleaved in the pancreatic cancer cells. FIG. 10 shows a time-dependent decrease in phospho-AKT (but not total AKT) in the pancreatic cancer cell lines, but not in the HPDE cells.

Figure 11A:
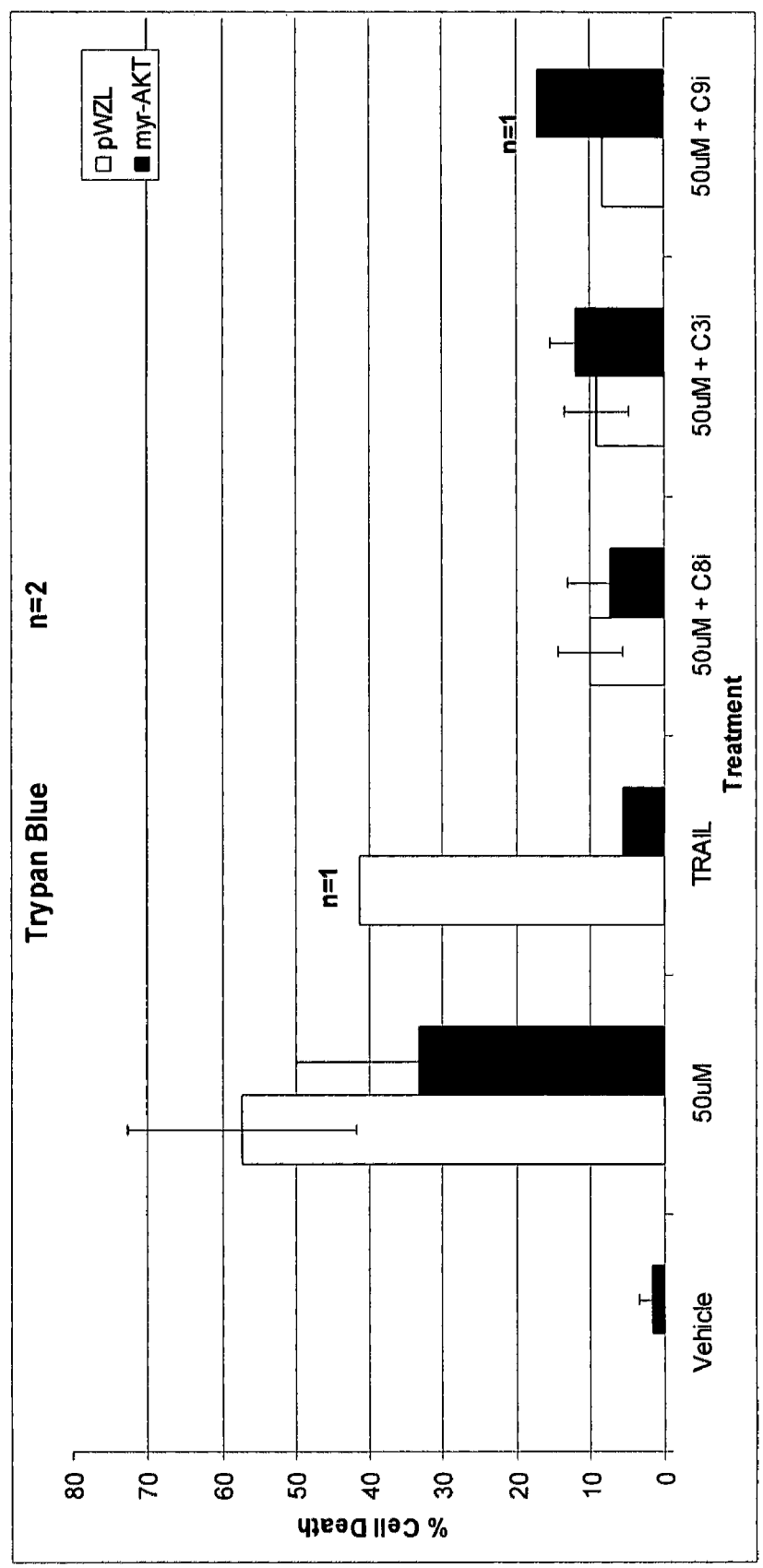
FIG. 11A is a graph wherein MIA PaCa-2 cells (pZWL vector and myrAKT) were treated without serum vehicle or δ-tocotrienol (50 μM) for 24 hours, with and without a 10-hour caspase 8/3 inhibitor pretreatment. Cells were also treated with TRAIL as a positive control. Cells were then harvested, fixed, permeablized and stained with trypan blue. The graph shows a significant increase in apoptotic cells in vector compared to vehicle, myr-AKT, or caspase 8/3 inhibitor treated cells.
Figure 11B:
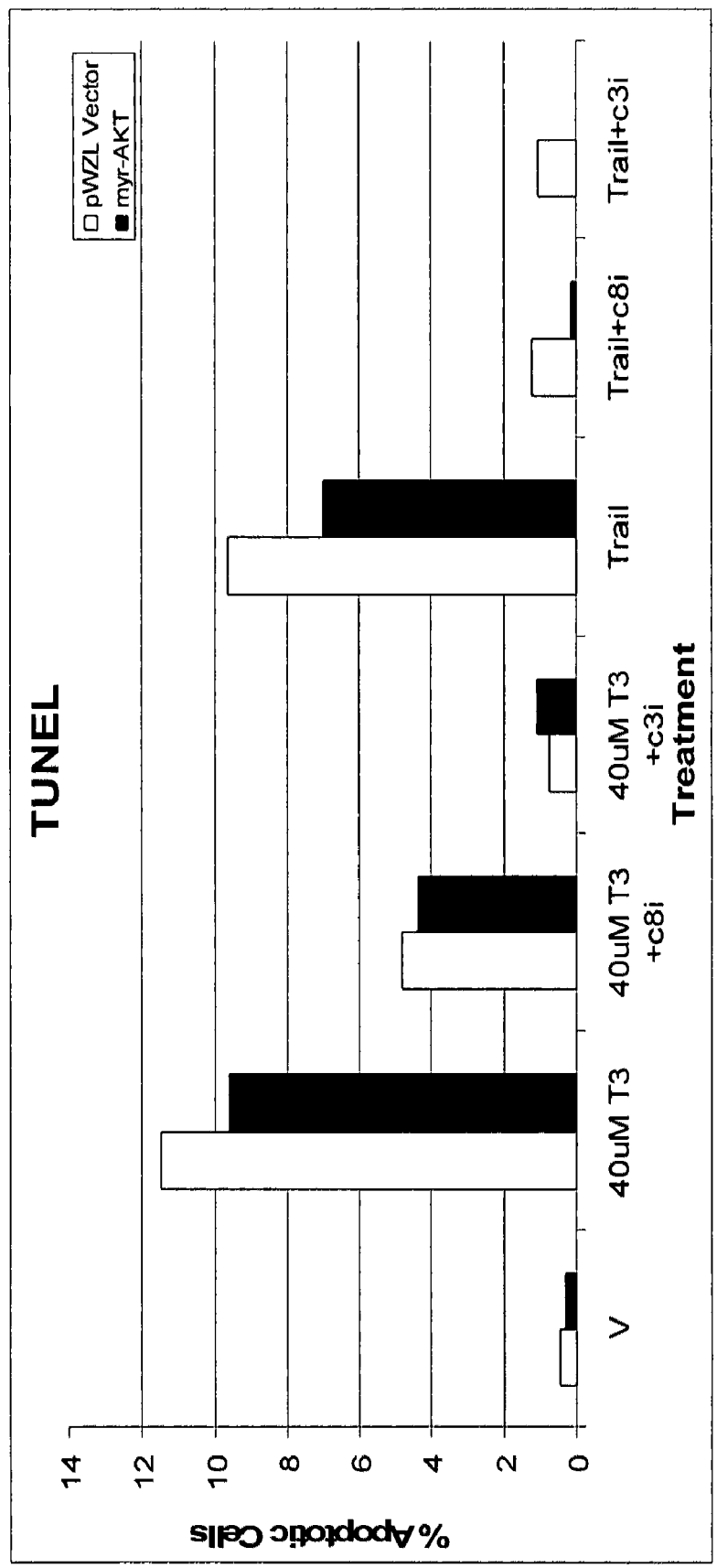
FIG. 11B is a graph wherein MIA PaCa-2 cells (pZWL vector and myrAKT) were treated without serum vehicle or δ-tocotrienol (40 μM) for 24 hours, with and without a 10-hour caspase 8/3 inhibitor pretreatment. Cells were then harvested, fixed, permeablized and stained for Tunel. The graph shows a significant increase in apoptotic cells in vector compared to vehicle, myr-AKT, or caspase 8/3 inhibitor treated cells.

The functional overexpression of CA-AKT demonstrates the role of AKT signaling and caspase 8 in δ-Tocotrienol-induced cell death (FIG. 11A). MIA PaCa-2 cells (pZWL vector and myrAKT) were treated without serum vehicle or δ-tocotrienol (40 or 50 μM) for 24 hours, with and without a 10-hour caspase 8 inhibitor pretreatment. Cells were also treated with TRAIL as a positive control. Cells were then harvested, fixed, permeablized and stained with trypan blue. Western blot (FIG. 11B) of cell lysates from FIG. 11A demonstrate the decrease of pAKT with 50 uM treatment of tocotrienol in MiaPaca 2 parenteral cells transfected with empty vector compared to cells overexpressing constitutively active AKT.

Figure 12B:
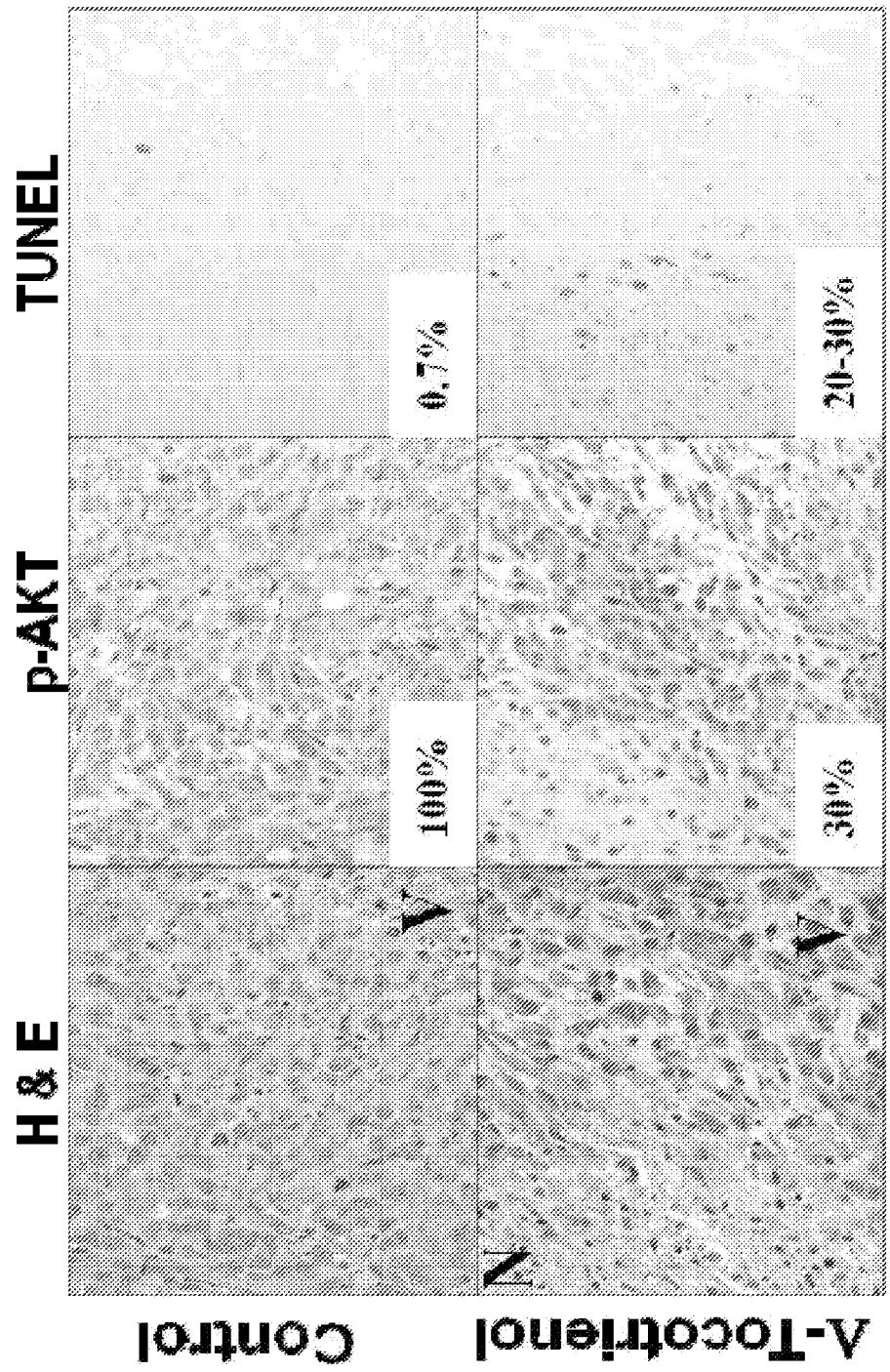
FIG. 12B Immunohistochemical staining demonstrates δ-tocotrienol induced apoptosis as measured by TUNEL staining, and decreased p-AKT expression.

MIA PaCa2 xenografts in nude mice were measured every second day for tumor growth. Mice were treated with either rice bran oil (vehicle) or δ-tocotrienol (100 mg/kg/day) via gavage five times per week. Results (FIG. 12A) demonstrate significant inhibition of pancreatic tumor growth in mice treated with δ-tocotrienol. Immunohistochemical staining (FIG. 12B) demonstrates δ-tocotrienol induced apoptosis as measured by TUNEL staining, and decreased p-AKT expression.

Figure 13A:
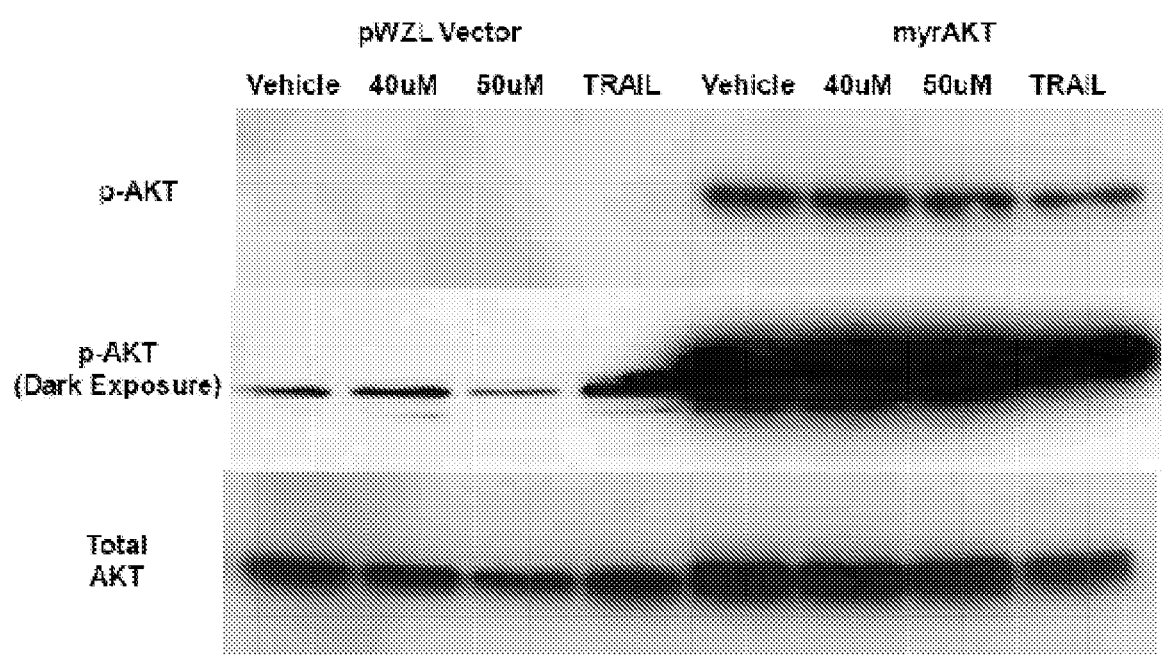
FIG. 13A is a series of blots demonstrating the rescue of δ-Tocotrienol suppression PI3K-AKT signaling after infection of Mia-PaCa2 pancreatic cancer cells with pWZL retroviral vector encoding myristoylated AKT.
Figure 13B:
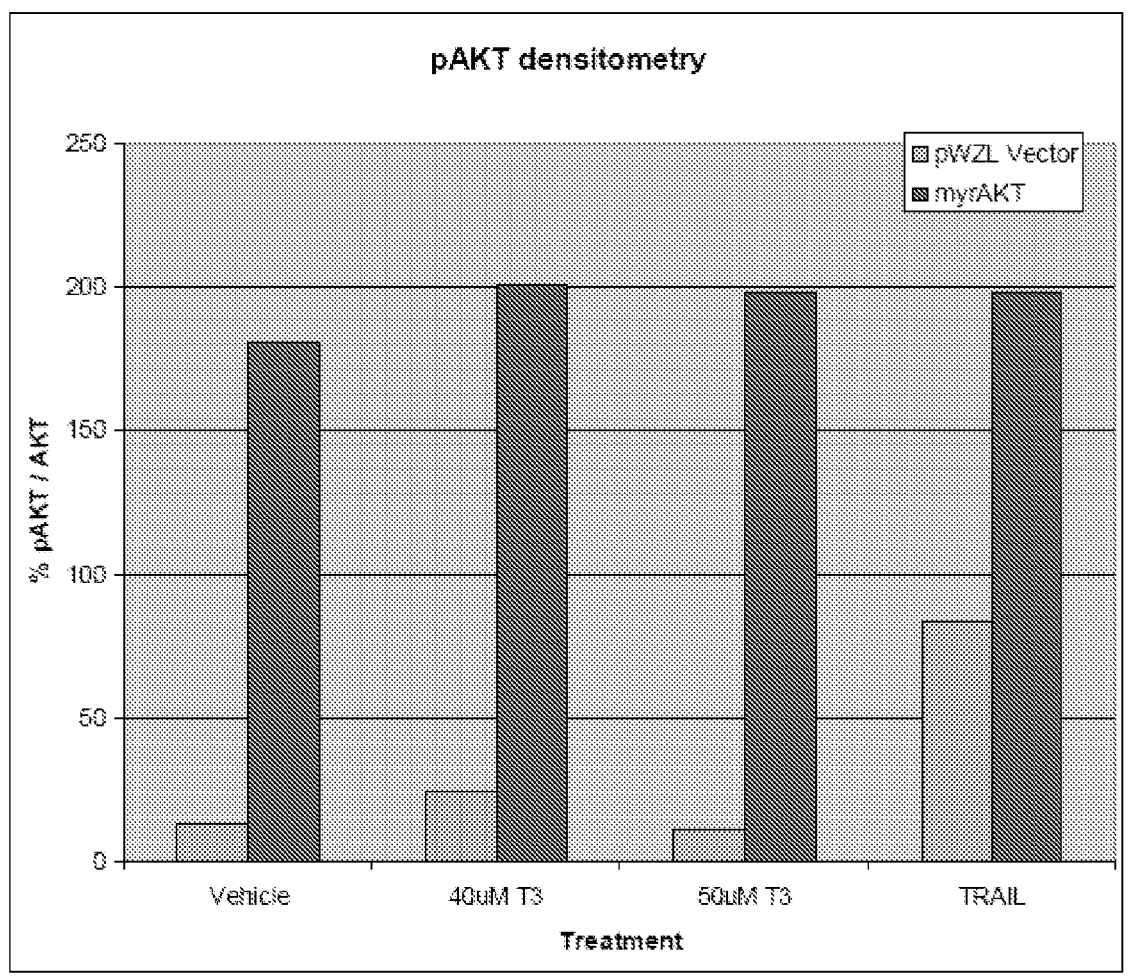
FIG. 13B is a graph of pAKT densitometry, demonstrating the rescue of δ-Tocotrienol suppression PI3K-AKT signaling after infection of Mia-PaCa2 pancreatic cancer cells with pWZL retroviral vector encoding myristoylated AKT.
Figure 13C:
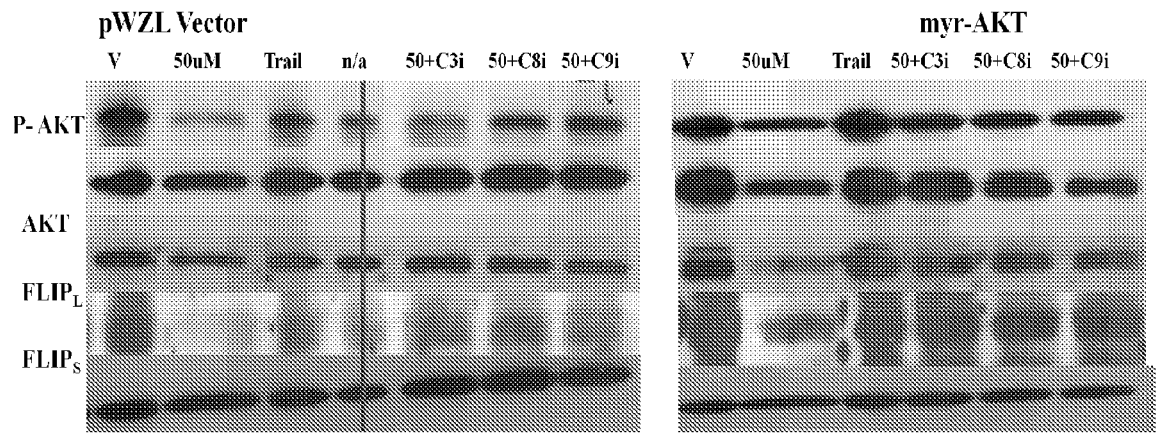
FIG. 13C is a series of blots showing that delta-tocotrienol modulates AKT signaling. Mia-PaCa2 pancreatic cancer cells with pWZL retroviral vector encoding myristoylated AKT.
Figure 13D:
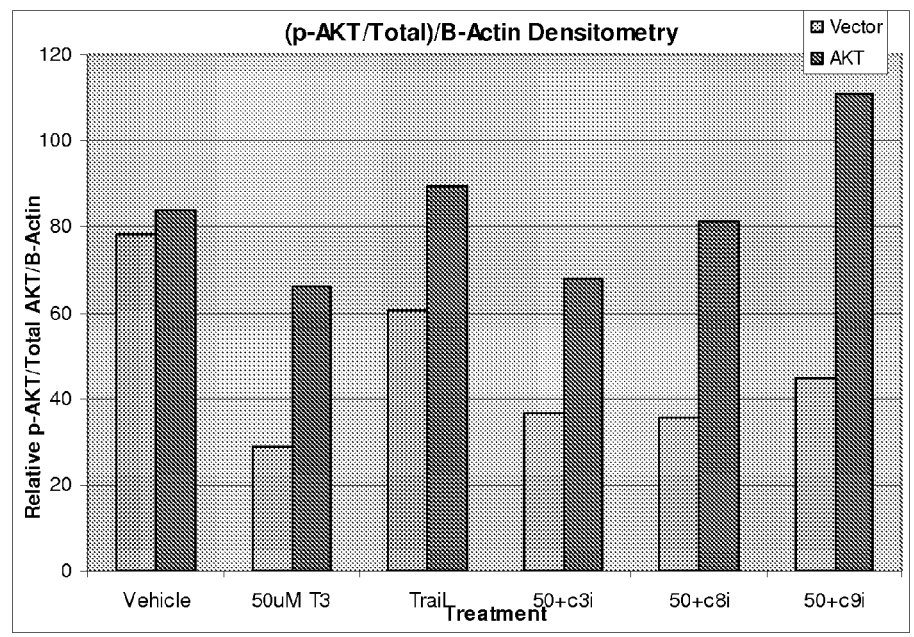
FIG. 13D is a graph showing (p-AKT/Total)/B-actin densitometry.
Figure 13E:
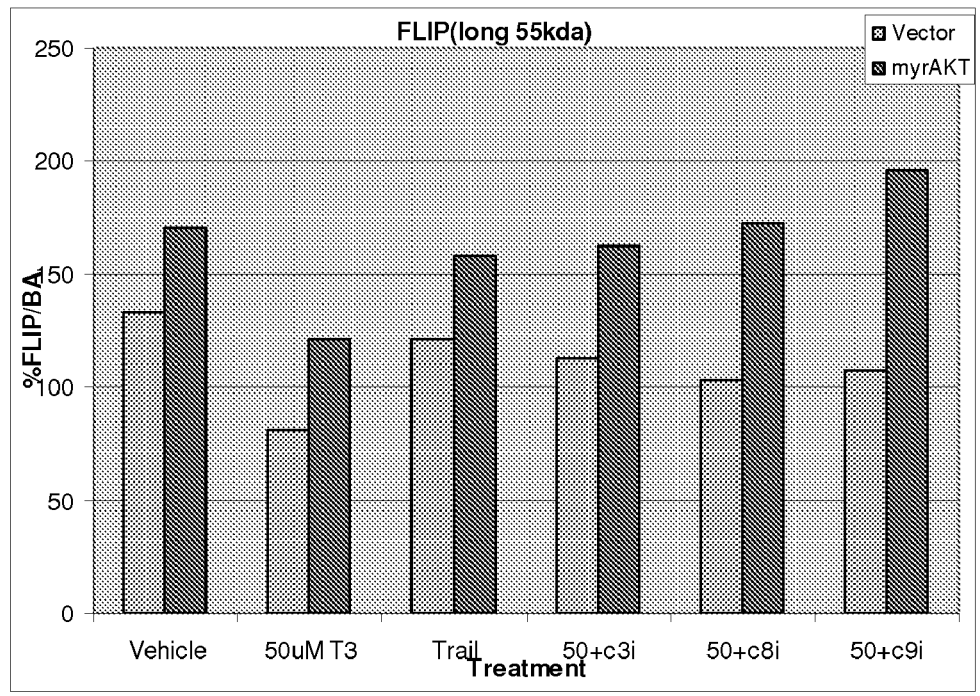
FIG. 13E is a graph showing % FLIP(long 55 kda)/B-actin densitometry.
Figure 13F:
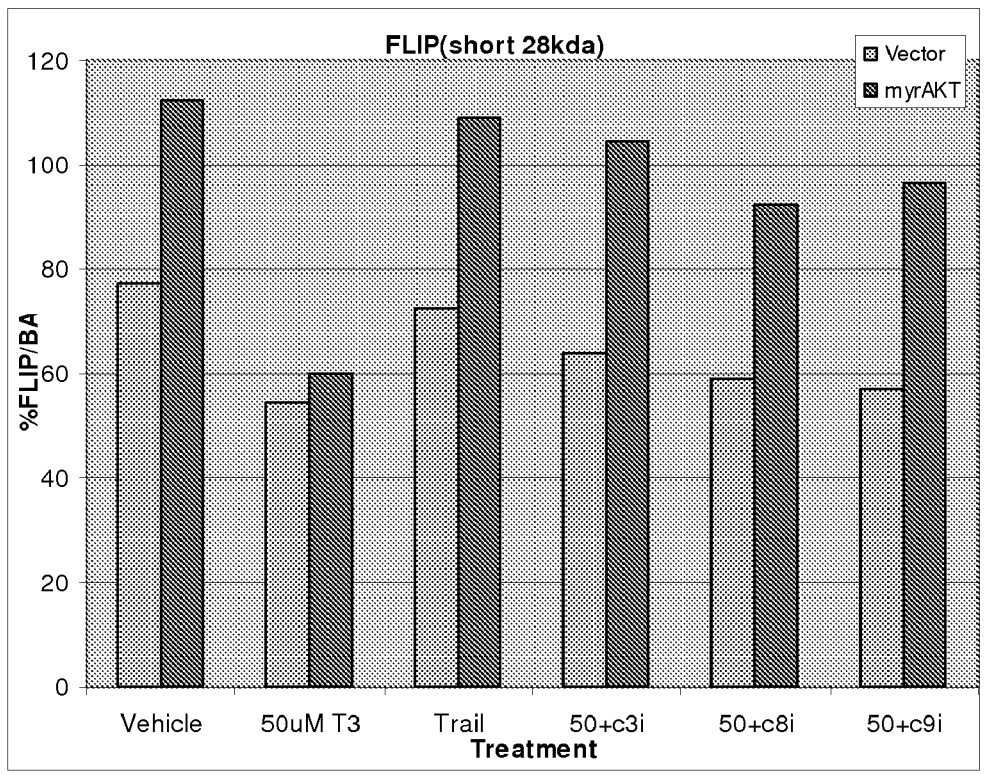
FIG. 13F is a graph showing % FLIP(short 28 kda)/B-actin densitometry.
Figure 13G:
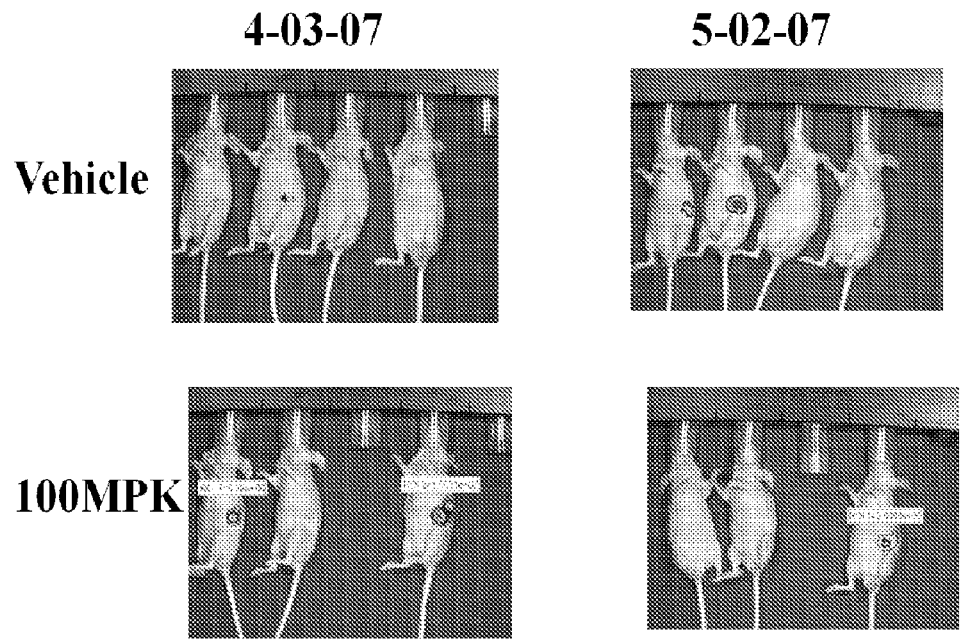
FIG. 13G are saturated luminescent images of in vivo results showing delta-tocotrienol inhibits pancreatic cancer metastasis. Images show comparison of vehicle vs. 100 MPK
Figure 13H:
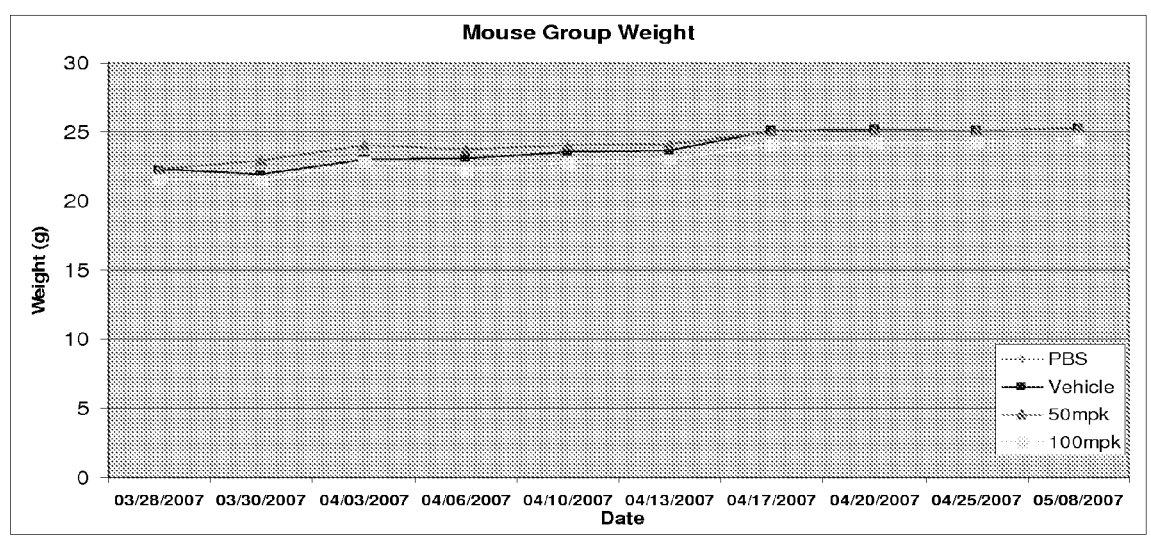
FIG. 13H is graph quantification of tumor metastasis by mouse weight group.
Figure 13I:
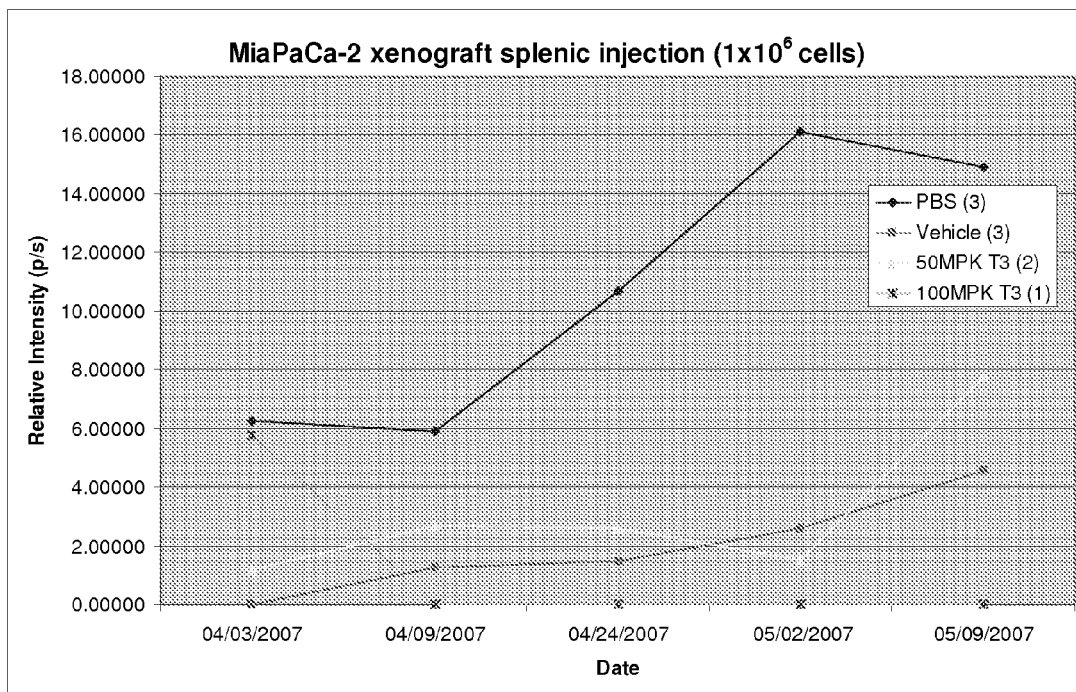
FIG. 13I is a graph showing the relative intensity (p/s)/time for PBS, vehicle, 50 MPK (T3), 100 MPK(T3).
Figure 13J:
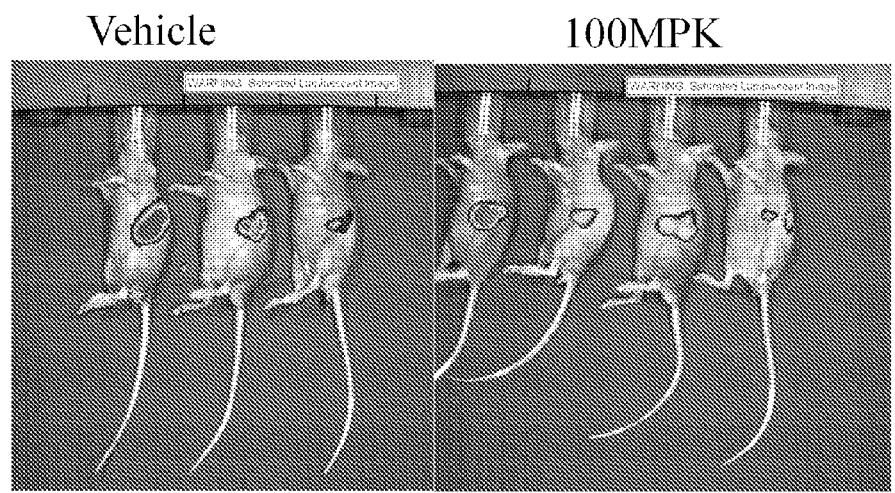
FIG. 13J saturated photoluminescent images of the accumulation of tocotrienol in mouse pancreas.

Moreover, infection of Mia-PaCa2 pancreatic cancer cells with pWZL retroviral vector encoding myristoylated AKT demonstrates rescue of δ-Tocotrienol suppression PI3K-AKT signaling. MiaPaCa-2 parental cell lines were stably transfected using a retroviral pWZL vector construct expressing constitutively active myristoylated AKT to generate Mia-PaCa-2$_{AKT}$ cells. FIGS. 13A and 13B demonstrate the rescue of δ-tocotrienol's ability to downregulate p-AKT.

FIGS. 13C through 13F show the AKT and caspase 8/3 pathways are involved in the mechanism by which tocotrienol induces cell death. Treatment with tocotrienol induced more cell death in the vector cells than the myr-AKT cells when compared to vehicle. TRAIL induced cell death was comparable to vehicle. Lastly, pretreatment with caspase 3, 8 and 9 inhibitors rescued tocotrienol induced cell death.

Delta-tocotrienol inhibits pancreatic cancer metastasis as shown in FIGS. 13G-13J. Tocotrienol caused tumor regression at the highest dose compared to vehicle/PBS. Accordingly, tocotrienol inhibits pancreatic tumor growth in vivo.

Figure 13K:
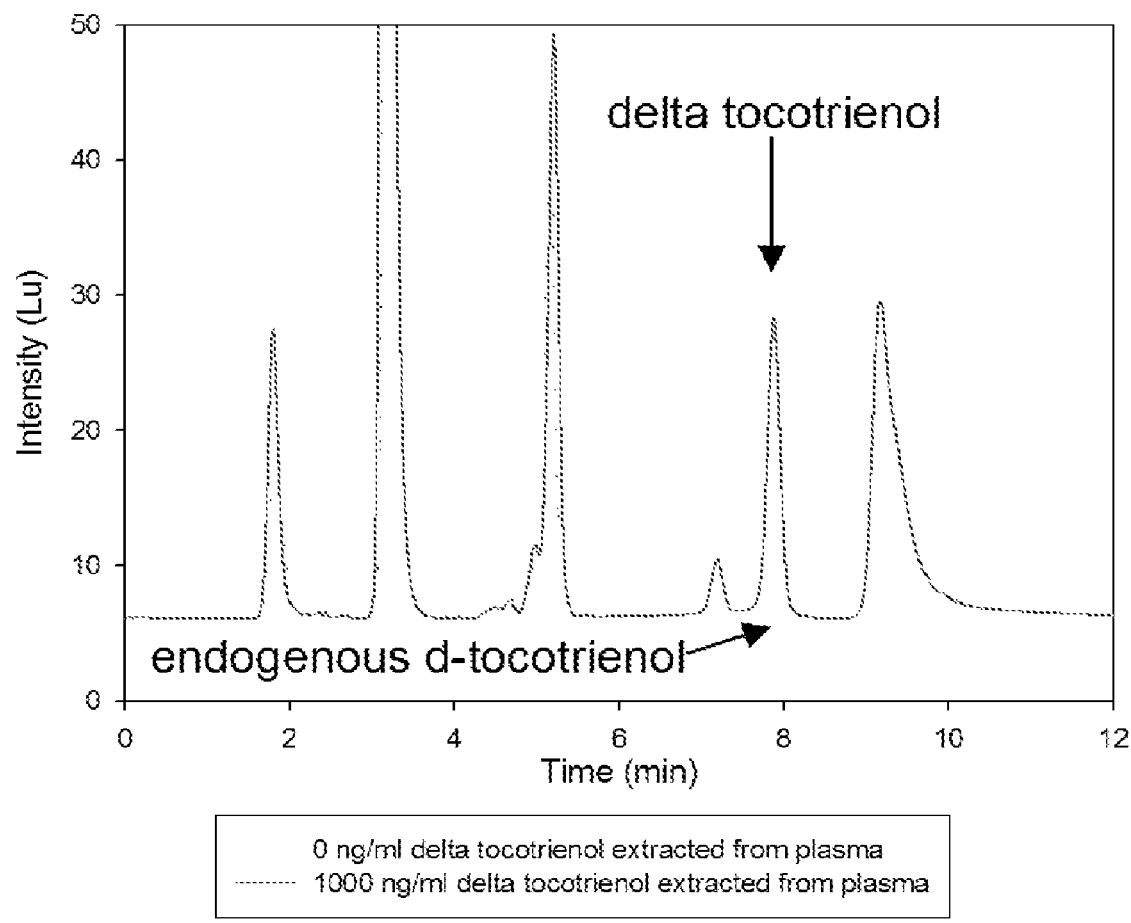
FIG. 13K is a chromatogram comparing blank plasma versus spiked plasma with delta tocotrienol after precipitation and extraction.
Figure 13L:
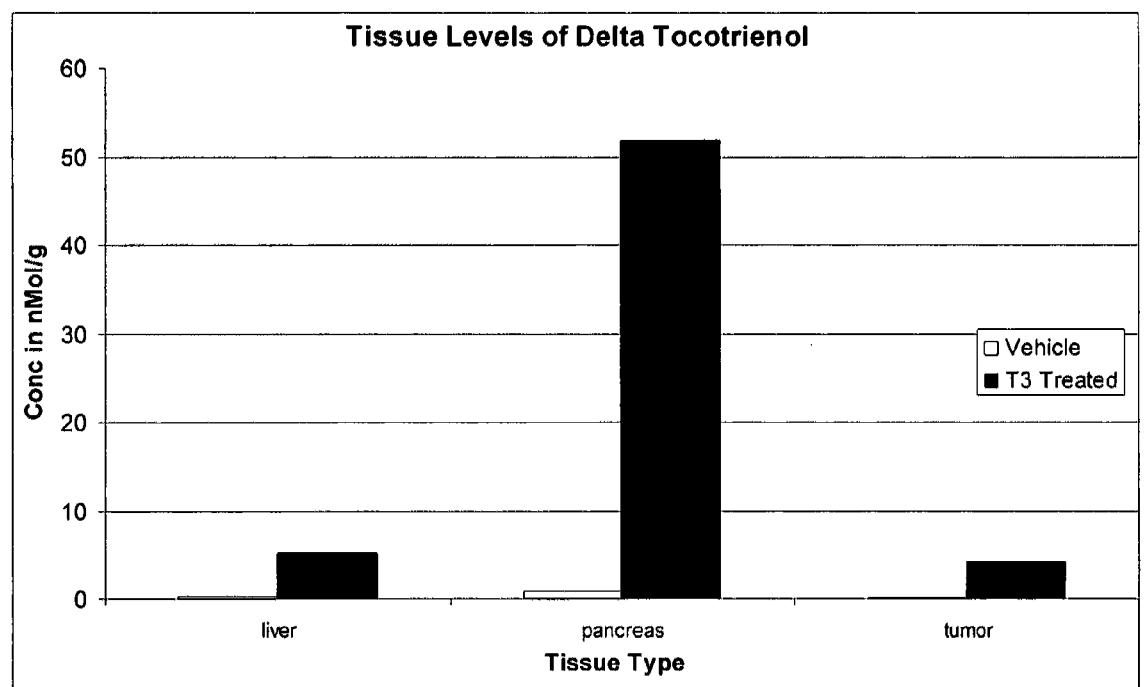
FIG. 13L is a graph showing tissue levels of delta-tocotrienol.

Putative cancer chemoprevention in plasma and mouse tissue by HPLC-UV via vitamin E and delta-tocotrienol is shown in FIGS. 13K and 13L. Tocotrienol was detectable in plasma and was significantly concentrated in the pancreas. Surprisingly, tocotrienol localizes in the pancreas by a factor of 10 when compared to liver and tumor levels. These results indicate the mechanism for tocotrienol action.

Taken together, these findings show δ-Tocotrienol selectively induces apoptosis in pancreatic cancer cell via the extrinsic apoptotic pathway. δ-Tocotrienol selectively inhibits the PI3-K/AKT pathway and induces apoptosis in vivo and this is associated with inhibition of AKT signaling targets. Moreover, overexpression of myr AKT in Pancreatic Cancer cells rescues the effect δ-Tocotrienol induces apoptosis in vitro and in vivo. Also, tocotrienol inhibition of pancreatic cancer cell growth can be rescued by constitutively active myrAKT. This suggests that tocotrienol induces apoptosis in pancreatic cancer at the level of pAKT.

It can be seen that delta-tocotrienol induced apoptosis of pancreatic cancer cells likely involves modulation of the Akt signaling pathway, because the Akt survival signaling pathway is often overexpressed in pancreatic cancer and implicated in non-mitochondria associated apoptosis. Delta-tocotrienol suppressed the phosphorylation levels of serine/threonine kinase Akt in vitro and in vivo. Furthermore, overexpression of constitutively active Akt protected pancreatic cancer cells from undergoing apoptosis after incubation with delta-tocotrienol. Together, these data indicate that delta-tocotrienol induces apoptosis in pancreatic cancer cells through activation of the caspase 8 cascade and suppression of the Akt survival pathway and shows that this micronutrient is useful for pancreatic cancer chemoprevention and treatment in vivo.

Surrogate End Point Biomarkers for Pancreatic Cancer

Historically, the chemopreventive benefit of an agent could only be shown by a reduced cancer incidence or mortality. The use of reduced incidence or mortality as end points makes chemoprevention trials long, large, costly, and, hence impractical except for cancers that have high event rates. Indeed, the only reports of chemoprevention trials for pancreatic cancer have come from subset analysis of chemoprevention trials conducted for other indications. This approach has resulted in inconclusive observations of the value of agents such as α-tocopherol, β-carotene, aspirin, and non-steroidal anti-inflammatory drugs (NSAIDs).

Developing "early phase" clinical trial methodologies for chemopreventive agents akin to the phase I and phase II studies for traditional cancer therapeutics is an important research priority to advance chemopreventive drug development in pancreatic cancer. Ideally these studies should confirm not only the potential for chemoprevention, but also answer questions about optimal dose and schedule. In response to these challenges, several investigators have proposed and initiated studies that focus on candidate surrogate end point biomarkers (SEBs) of the target lesion pathophysiology rather than on long-term cancer prevention.

In SEB trials, reduction in tumor incidence is replaced with evidence for reversal of one or more elements of the neoplastic phenotype, such as abnormal proliferation, cell survival, or aberrant gene expression. Specifically, these strategies focus on the effect of agents on a significant precancerous lesion, intraepithelial neoplasia (IEN). Whereas IEN is a validated precancer in most epithelial tissues, mucinous cystic neoplasms (MCNs), intraductal papillary mucinous neoplasms (IPMNs), and pancreatic intraepithelial neoplasia (PanIN), are the best-characterized IENs in pancreatic tissue. The progress of these lesions to invasive carcinoma is well characterized and surgical removals of these lesions are already recommended medical practice for prevention of pancreatic cancer.

Although SEB studies are well established in the setting of IENs that do not require surgical intervention, such as leukoplakia of the oral mucosa or Barrett's esophagus, such studies are more difficult to conduct in premalignant lesions requiring immediate surgical intervention because the index lesion is removed and is not amenable to subsequent follow-up. However, the need for sequential procedures to diagnose and remove invasive and preinvasive pancreatic lessions, provides an opportunity for short-term SEB studies. An interval of two to four weeks is standard in most practices, hence offering a window within which a chemopreventive agent can be administered to evaluate the effects of the agent on SEB modulation. The inventor's experiments show the value of standard SEBs such as proliferation rate, apoptosis index, and the expression of proteins (discussed below) that are modulated by the early genetic changes in these lesions.

In one embodiment, the invention includes surrogate endpoint biomarkers that were prevelant in the surgical specimens of patients who have undergone resection of invasive ductal adenocarcinomas of the pancreas (IPMNs). Tocotrienol, such as δ-tocotrienol from annatto bean, demonstrated selectively inhibition in human pancreatic cancer cells. The data shows that δ-tocotrienol affects a number of molecular processes including induction of apoptosis and inhibition of tumor growth and that δ-tocotrienol inhibits oncogenic signal transduction pathways in pancreatic neoplastic cells. Specifically, δ-tocotrienol decreases phospho-Raf, phospho-MEK, phospho-ERK, and phospho-AKT levels in human pancreatic cancer cells. Furthermore, δ-tocotrienol induces the expression of growth inhibitory mediators such as $p27^{Kip1}$, and activates the apoptotic mediators caspase 8 and caspase 3.

Cases of resected pancreatic ductal carcinoma from 1986 to 2006 were collected from the Moffitt Cancer Center Tumor Registry and Pathology information system. Slides from each case were reviewed by a single pathologist for histological tumor type, grade, and presence of ductal precursor lesions. Histologic type and grade were assigned based on current W.H.O nomenclature. Pancreatic carcinoma precursor lesions, termed pancreatic intraepithelial neoplasia (PanIN) were graded Ia, Ib, 2, and 3 according to published criteria (Hruban, 2001). Based on slide review, 10 representative tissue blocks were selected from ten consecutive resection specimens. Preference was given to sections showing carcinoma, (preferably more than one grade of carcinoma), non-neoplastic ducts, and precursor lesions. All cases were ductal adenocarcinoma, NOS, or well to poorly differentiated.

Figure 14A:
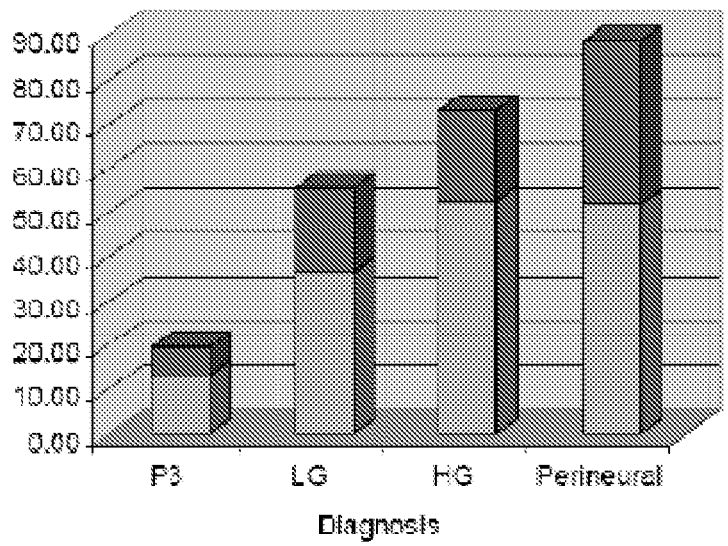
FIG. 14A is a graph showing an increase in proliferation rate as the degree of invasion and grade of tumor is increased. This is indicated by a progressive increase in the mean percentage of cells staining positive for Ki-67.
Figure 14B:
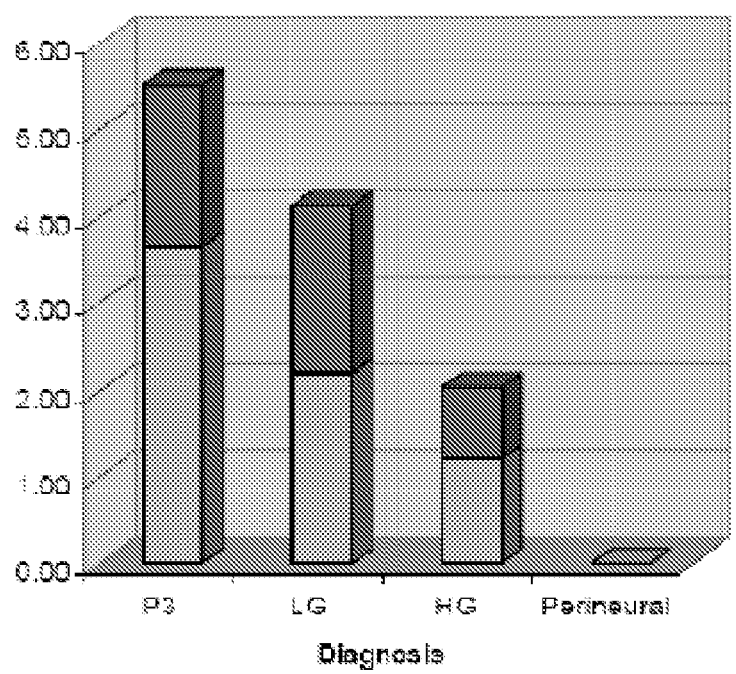
FIG. 14B is a graph showing a progressive decrease in the number of apoptotic cells stained with TUNEL, negatively correlating with the degree of tumor invasion.
Figure 15:
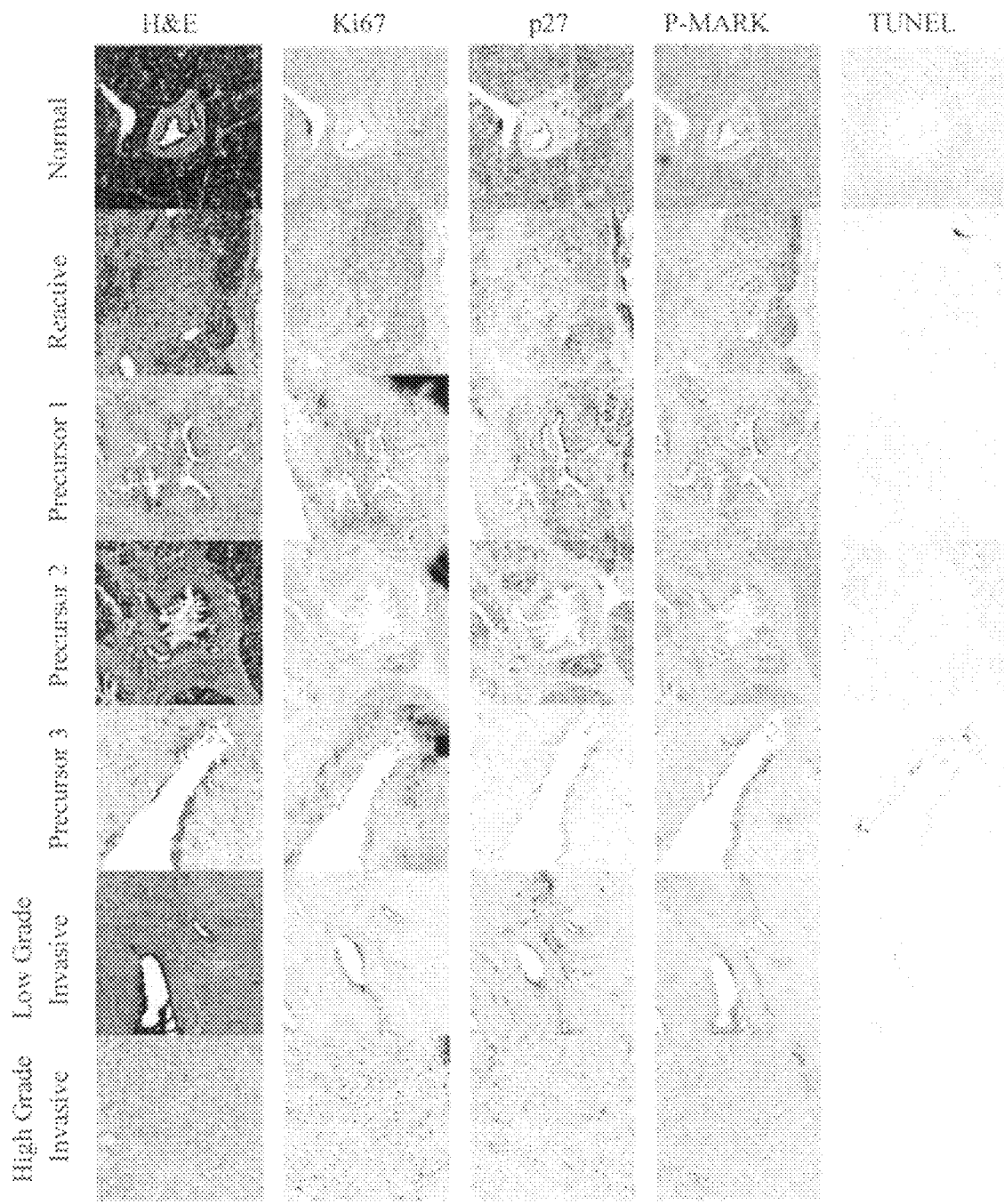
FIG. 15 is a series of representative slides of non-neoplastic pancreatic ductal tissue, reactive tissue, precursor lesions (PanIN 1-3), and low and high grade invasive carcinomas. Each representative area was stained with Hematoxylin and Eosin, and for Ki-67, p27, p-MAPK, and TUNEL. Results show an increase in Ki-67 and p-MAPK staining as pancreatic ducts progress from nonneoplastic to PanIN to invasive carcinoma. The greatest degree of staining is in high grade tumors. In contrast p27 and TUNEL staining decrease with tumor invasiveness and progression. Indicating a loss of cell cycle inhibition and induction of apoptosis.

The data shown in FIGS. 14A through 15 demonstrates the accuracy with which these intermediate biomarkers can be measured. Ki67 was noted to be a reliable marker of proliferation with progressive increase of a positive reaction in the nucleus from normal to intermediate to invasive carcinoma. An inverse progression was noted for TUNEL staining indicating oncogenic suppression of apoptosis in neoplastic pancreatic ductal cells. A similar inverse progression was observed in the expression of the p27 cyclin-dependent kinase inhibitor protein. In contrast, downstream mediators of activated oncogenic Ras signaling such as phospho-MAPK and phospho-AKT are increased. Remarkably, all patients with invasive ductal cancer of the pancreas and IPMNs had noninvasive precursor lesions in their surgical specimens.

No cases of undifferentiated carcinoma or ductal adenocarcinoma variants were selected for this pilot study. One section was cut from each block for routine Hematoxylin and eosin stains. Sections cut for immunohistochemistry were placed on poly-L-lysine coated slides. Antibodies used included Ki-67, p27, and p-MAPK. A TUNEL assay was used to evaluate for apoptosis. Immunohistochemical studies were performed using standard immunohistochemical techniques. Slides were then scanned into the Ariol SL-50 (version 3.0.70) from Applied Imaging for accurate, reproducible, and objective high throughput analysis. Images were reviewed by one pathologist for representative areas of carcinoma, PanIN, reactive ducts, and non-neoplastic ducts. Well-differentiated and moderately differentiated carcinomas were grouped into one category of low grade for the purpose of this study. Poorly differentiated carcinoma was classified as high grade carcinoma. Additional areas of perineural invasion, if present on the slide, were also selected for analysis.

FIG. 14A shows an increase in proliferation rate as degree of invasion and grade of tumor is increased. This is indicated by a progressive increase in the mean percentage of cells staining positive for Ki-67. In contrast, FIG. 14B shows a progressive decrease in the number of apoptotic cells stained with TUNEL, negatively correlating with the degree of tumor invasion.

FIG. 15 shows representative slides of non-neoplastic pancreatic ductal tissue, reactive tissue, precursor lesions (PanIN 1-3), and low and high grade invasive carcinomas. Each representative area was stained with Hematoxylin and Eosin, and for Ki-67, p27, p-MAPK, and TUNEL.

Results show an increase in Ki-67 and p-MAPK staining as pancreatic ducts progress from non-neoplastic to PanIN to invasive carcinoma. The greatest degree of staining is in high grade tumors. In contrast p27 and TUNEL staining decrease with tumor invasiveness and progression. Indicating a loss of cell cycle inhibition and induction of apoptosis.

Another embodiment of the invention includes a method of screening for pancreatic ductal carcinoma, or a stage of pancreatic cancer in a subject by determining, such as in an isolated sample, the level of a biomarker; namely, p27. The level of the biomarker is then compared to a corresponding control level in one or more control samples. In a preferred embodiment the control samples are obtained from individuals who have been determined not to have pancreatic ductal carcinoma, or a stage of pancreatic cancer.

The determination of a statistically significant increase between the level of the biomarker in the subject and the level of the biomarker in the control sample(s) is indicative of the lack of pancreatic ductal carcinoma, or a stage of pancreatic cancer in the subject. A statistically significant decrease in the level of p27 in the subject, compared to the level of the biomarker in the control sample(s), indicates the presence of pancreatic ductal carcinoma, or a stage of pancreatic cancer in the subject.

In an alternate embodiment, the level of a second biomarker, namely Ki-67 and/or p-MAPK, is determined and compared to a control level of Ki-67 and/or p-MAPK in one or more control samples. A statistically significant increase between the level of Ki-67 and/or p-MAPK in the subject and the control sample(s) is indicative of pancreatic ductal carcinoma, or a stage of pancreatic cancer in the subject. A statistically significant decrease in the level of Ki-67 and/or p-MAPK in the subject, compared to the control sample(s), is indicative of the lack of pancreatic ductal carcinoma, or a stage of pancreatic cancer in the subject.

Methods of determining the level of the biomarker in the subject and control sample(s) are known to the ordinary practitioner. In one embodiment, as an example, the level of the biomarker is determined utilizing an antibody which binds the biomarker. The sample containing the biomarker is contacted with the antibody under conditions which allow binding of the biomarker to the antibody; the presence of the biomarker can then be quantified.

The invention also includes compositions useful in performing the associated methods. For example, the invention includes a composition comprising a plurality of isolated proteins which bind selectively to the protein products of the associated biomarkers; namely, Ki-67 and/or p-MAPK, and p27. In a preferred embodiment, the isolated proteins selectively amplify complementary double stranded DNA. A composition is also included comprising a plurality of biomarker specific primers, wherein each biomarker specific primer selectively amplifies double stranded DNA complementary to a unique biomarker such as Ki-67, p-MAPK and p27. Alternatively, the invention includes a composition comprising a plurality of isolated proteins which bind selectively to the protein products of at least two unique biomarkers, wherein each unique biomarker is selected from the group consisting of Ki-67, p-MAPK and p27.

As used herein, the term "biomarker" refers to a gene that is differentially expressed in individuals having cancer, including pancreatic cancer or a stage of pancreatic cancer as compared with those not having cancer, including pancreatic or a stage of pancreatic cancer. The term "biomarker" can include a gene that is differentially expressed in individuals having superficial pancreatic cancer as compared with those not having pancreatic cancer.

The term "biomarker specific primers" as used herein refers to a set of primers which can produce double stranded DNA complementary to a portion of one or more RNA products of the biomarker of the invention. For example, the primers can include a first primer which is a sequence that can selectively hybridize to RNA, cDNA or EST complementary to a biomarker of the invention to create an extension product and a second primer capable of selectively hybridizing to the extension product, which are used to produce double stranded DNA complementary to a biomarker of the invention.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art. In general, the design and selection of primers embodied by the instant invention is according to methods that are standard and well known in the art, see Dieffenbach, C. W., Lowe, T. M. J., Dveksler, G. S. (1995) General Concepts for PCR Primer Design. In: PCR Primer, A Laboratory Manual (Eds. Dieffenbach, C. W, and Dveksler, G. S.) Cold Spring Harbor Laboratory Press, New York, 133-155; Innis, M. A., and Gelfand, D. H. (1990) Optimization of PCRs. In: PCR protocols, A Guide to Methods and Applications (Eds. Innis, M. A., Gelfand, D. H., Sninsky, J. J;, and White, T. J.) Academic Press, San Diego, 3-12; Sharrocks, A. D. (1994) The design of primers for PCR. In: PCR Technology, Current Innovations (Eds. Griffin, H. G., and Griffin, A. M, Ed.) CRC Press, London, 5-11.

The term "biomarker specific probe" as used herein refers to a probe selectively and specifically hybridizes to RNA products of a unique biomarker. In one embodiment a biomarker specific probe can be a probe having a fluorophore and a quencher, for example a TaqMan® probe or a Molecular Beacons probe. In another embodiment a biomarker specific probe is a probe which is attached to an array and selectively and specifically hybridizes to one or more RNA products (or cDNA, EST or PCR products corresponding to said RNA products) of a unique biomarker. A biomarker specific probe can include oligonucleotide probes and can also include longer probes (e.g. 60, 80, 100, 150, 200, 250, 300, 350, 400, 450, 500 Nucleotides etc.).

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length. Probes can include oligonucleotides modified so as to have a tag which is detectable by fluorescence, chemiluminescence and the like. The probe can also be modified so as to have both a detectable tag and a quencher molecule, for example Taqman® and Molecular Beacon® probes.

As used herein, the term "product of the biomarker" or "biomarker product" refers to the RNA or protein which corresponds or is encoded by the biomarker (i.e. is transcribed from the gene or genetic element or is translated from RNA which is transcribed from the gene or genetic element). For example, in some embodiments RNA resulting from the biomarker can include one or more of the following species; hnRNA, mRNA, and/or one or more spliced variants of mRNA. In some embodiments, proteins resulting from the molecular marker can include any proteins found in blood which correspond to the RNA resulting from the biomarker.

As used herein, the term "control" or "control sample" in the context of this invention refers to one or more tissue nucleic acid samples and/or a blood nucleic acid samples and/or one or more individuals who are classified as having pancreatic cancer, having one or more stages of pancreatic cancer and/or superficial bladder cancer; not having pancreatic cancer, having one or more stages of pancreatic cancer and/or superficial bladder cancer; as determined by using those techniques known to a person skilled in the art. The term control or control sample can also refer to the compilation of data derived from samples of one or more individuals who have been diagnosed as normal (not having pancreatic cancer), having pancreatic cancer, or having a stage of pancreatic cancer. As would be understood by a person skilled in the art—the term control is used in the context of the experiment and will depend upon the desired comparisons. As used herein, the term "control" in the context of screening for a prophylactic or therapeutic agent refers to a standard or reference for an assay or methodology to which other conditions can be compared.

As used herein, the term "effective amount" refers to the amount of a compound which is sufficient to reduce or ameliorate the progression and or severity of pancreatic cancer or one or more symptoms thereof, prevent the development, recurrence or onset of pancreatic cancer or one or more symptoms thereof, prevent the advancement of pancreatic cancer or one or more symptoms thereof, or enhance or improve the prophylactic or therapeutic effect(s) of another therapy.

As used herein, the terms "chemotherapeutic agent" refers to any compound(s) which can be used in the treatment, management or amelioration of pancreatic cancer or one or more symptoms thereof.

As used herein, the term "therapeutically effective amount" refers to that amount of a therapy (e.g., a chemotherapeutic agent) sufficient to result in the amelioration of pancreatic cancer or one or more symptoms thereof, prevent advancement of bladder cancer cause regression of bladder cancer, or to enhance or improve the therapeutic effect(s) of another therapy (e.g., chemotherapeutic agent).

As used herein, the term "efficacy" refers to the effectiveness of a drug and/or "Chemotherapeutic efficacy" is usually measured by the clinical response of the patient who has been or is being treated with a drug and/or agent. A drug is considered to have a high degree of efficacy, if it achieves desired clinical results, for example, the reduction of the symptoms associated with pancreatic cancer, a stage of pancreatic cancer, or the prevention of pancreatic cancer progression as described in the present specification. The amount of drug absorbed may be used to predict a patient's response. A general rule is that as the dose of a drug is increased, a greater effect is seen in the patient until a maximum desired effect is reached.

As used herein, the term "level of expression" refers to the determination of the quantity of a given nucleic acid or protein corresponding to a gene as determined by methods known to a person skilled. In reference to RNA, hnRNA, mRNA or spliced variants of mRNA corresponding to a biomarker of the invention, level of expression can be determined by hybridization as well as other measurements such as quantitative real-time RT PCR, which includes use of SYBR® green, TaqMan® and Molecular Beacons technology. Note that as used herein the determination of differential levels of expression can include a visual inspection of differences as between the quantity of a given nucleic acid or protein, for example by analyzing the northern blot or western blot.

As used herein, the term "selectively amplified" or "selective amplification", refers to a process whereby one or more copies of a particular target nucleic acid sequence is selectively generated from a template nucleic acid. Selective amplification or selectively amplified is to be compared with amplification in general which can be used as a method in combination with, for example, random primers and an oligodT primer to amplify a population of nucleic acid sequences (e.g. mRNA). Selective amplification is preferably done by the method of polymerase chain reaction (Mullis and Faloona, 1987, Methods Enzymol. 155:335).

As used herein, the term "selectively binds"in the context of proteins encompassed by the invention refers to the specific interaction of any two of a peptide, a protein, a polypeptide, and an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognizes and binds to a structure on the second molecule, rather than to other proteins. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

Therefore, in one embodiment, the invention includes a method of determining the effectives of a chemotherapeutic agent by determining, in an isolated sample, a first level of a surrogate endpoint biomarker such as p27. The sample is then contacted with an experimentally effective amount of the chemotherapeutic agent being tested. After the chemotherapeutic agent has been administered, a second level of the surrogate endpoint biomarker is taken and compared to the first (pre-treatment) level. The candidate chemotherapeutic agent demonstrates effectiveness where the second (post-treatment) levels p27 are increased to a statistically significant degree over the pre-treatment and/or control levels.

In another embodiment, the invention provides a method of determining the effectives of a chemotherapeutic agent by further determining, in the isolated sample, a first level of a second surrogate endpoint biomarker such as Ki-67 and/or p-MAPK. After the chemotherapeutic agent has been administered, a second level of Ki-67 and/or p-MAPK is taken and compared to the first (pre-treatment) level and/or a control. The candidate chemotherapeutic agent demonstrates effectiveness where the second (post-treatment) levels of Ki-67 and/or p-MAPK are decreased to a statistically significant degree below the pre-treatment and/or control levels.

Another embodiment of the invention includes a method of screening for pancreatic ductal carcinoma, or a stage of pancreatic cancer in a subject by determining, such as in an isolated sample, the level of a biomarker; namely, p27. The level of the biomarker is then compared to a corresponding control level in one or more control samples. In a preferred embodiment the control samples are obtained from individuals who have been determined not to have pancreatic ductal carcinoma, or a stage of pancreatic cancer.

The determination of a statistically significant increase between the level of the biomarker in the subject and the level of the biomarker in the control sample(s) is indicative of the lack of pancreatic ductal carcinoma, or a stage of pancreatic cancer in the subject. A statistically significant decrease in the level of p27 in the subject, compared to the level of the biomarker in the control sample(s), indicates the presence of pancreatic ductal carcinoma, or a stage of pancreatic cancer in the subject.

In an alternate embodiment, the level of a second biomarker, namely Ki-67 and/or p-MAPK, is determined and compared to a control level of Ki-67 and/or p-MAPK in one or more control samples. A statistically significant increase between the level of Ki-67 and/or p-MAPK in the subject and the control sample(s) is indicative of pancreatic ductal carcinoma, or a stage of pancreatic cancer in the subject. A statistically significant decrease in the level of Ki-67 and/or p-MAPK in the subject, compared to the control sample(s), is indicative of the lack of pancreatic ductal carcinoma, or a stage of pancreatic cancer in the subject.

Methods of determining the level of the biomarker in the subject and control sample(s) are known to the ordinary practitioner. In one embodiment, as an example, the level of the biomarker is determined utilizing an antibody which binds the biomarker. The sample containing the biomarker is contacted with the antibody under conditions which allow binding of the biomarker to the antibody; the presence of the biomarker can then be quantified.

The invention also includes compositions useful in performing the associated methods. For example, the invention includes a composition comprising a plurality of isolated proteins which bind selectively to the protein products of the associated biomarkers; namely, Ki-67 and/or p-MAPK, and p27. In a preferred embodiment, the isolated proteins selectively amplify complementary double stranded DNA. A composition is also included comprising a plurality of biomarker specific primers, wherein each biomarker specific primer selectively amplifies double stranded DNA complementary to a unique biomarker such as Ki-67, p-MAPK and p27. Alternatively, the invention includes a composition comprising a plurality of isolated proteins which bind selectively to the protein products of at least two unique biomarkers, wherein each unique biomarker is selected from the group consisting of Ki-67, p-MAPK and p27.

Methods of determining the levels (e.g. quantifying) of the biomarkers will be readily known to one of ordinary skill and include, but are not limited to, determining expression level, level of RNA, level of RNA product, protein level, and/or protein activity level.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating pancreatic cancer, comprising administering to a subject a composition comprising a therapeutically effective amount of at least one tocotrienol, wherein the tocotrienol is at least one chemotherapeutic agent, wherein the chemotherapeutic agent is gemcitabine.

2. The method of claim 1 wherein the composition comprising a therapeutically effective amount of the tocotrienol is administered as a pharmaceutical composition.

3. The method of claim 1 wherein the composition is free of alpha-tocotrienol and beta-tocotrienol.

4. The method of claim 1 wherein the composition is free of at least one tocotrienol selected from the group consisting of alpha-tocotrienol and beta-tocotrienol.

5. The method of claim 1 wherein the composition is free of tocopherols.

6. The method of claim 1 wherein the composition comprises between about 100 mg to 300 mg of the at least one tocotrienol.

7. The method of claim 1 wherein the pancreatic cancer is pancreatic ductal carcinoma.

8. The method of claim 1 wherein the subject is selected from the group consisting of subjects with a genetic predisposition to pancreatic cancer and subjects with preneoplastic lesions.

9. The method of claim 8 wherein the preneoplastic lesions are selected from the group consisting of pancreatic intraepithelial neoplasia, intraductal papillary mucinous neoplasm, and mucinous cystic neoplasm.

* * * * *

UNITED STATES PATENT AND TRADEMARK OFFICE
CERTIFICATE OF CORRECTION

PATENT NO. : 8,288,369 B2
APPLICATION NO. : 11/768373
DATED : October 16, 2012
INVENTOR(S) : Mokenge P. Malafa et al.

It is certified that error appears in the above-identified patent and that said Letters Patent is hereby corrected as shown below:

In the Claims

In column 26, line 1, cancel the text "the tocotrienol is at least one chemotherapeutic agent" and insert the following:

--the tocotrienol is delta-tocotrienol and at least one chemotherapeutic agent--

Signed and Sealed this
Eleventh Day of November, 2014

Michelle K. Lee
*Deputy Director of the United States Patent and Trademark Office*